US012576225B2

(12) United States Patent
Martin

(10) Patent No.: US 12,576,225 B2
(45) Date of Patent: Mar. 17, 2026

(54) METHODS AND APPARATUS FOR CONTROLLING RESPIRATORY THERAPY

(71) Applicant: ResMed Pty Ltd, Bella Vista (AU)

(72) Inventor: Dion Charles Chewe Martin, Sydney (AU)

(73) Assignee: ResMed Pty Ltd (AU)

( * ) Notice: Subject to any disclaimer, the term of this patent is extended or adjusted under 35 U.S.C. 154(b) by 1020 days.

(21) Appl. No.: 17/270,209

(22) PCT Filed: Aug. 20, 2019

(86) PCT No.: PCT/AU2019/050875

§ 371 (c)(1),
(2) Date: Feb. 22, 2021

(87) PCT Pub. No.: WO2020/037361

PCT Pub. Date: Feb. 27, 2020

(65) Prior Publication Data

US 2021/0330913 A1 Oct. 28, 2021

(30) Foreign Application Priority Data

Aug. 23, 2018 (AU) ................................ 2018903109

(51) Int. Cl.
*A61M 16/00* (2006.01)
*A61M 16/10* (2006.01)
(52) U.S. Cl.
CPC ...... *A61M 16/022* (2017.08); *A61M 16/0003* (2014.02); *A61M 16/0063* (2014.02);
(Continued)
(58) Field of Classification Search
CPC .............. A61M 16/022; A61M 16/026; A61M 16/0069; A61M 16/101; A61M 16/0063;
(Continued)

(56) References Cited

U.S. PATENT DOCUMENTS 6,532,959 B1 3/2003 Berthon-Jones
2008/0119754 A1* 5/2008 Hietala ............... A61M 16/085
600/532
(Continued)

FOREIGN PATENT DOCUMENTS

WO 2011057362 A1 5/2011
WO 2015033288 A 4/2013
(Continued)

OTHER PUBLICATIONS

International Search Report mailed Nov. 29, 2019 for PCT/AU2019/050875.

(Continued)

*Primary Examiner* — Rachel T Sippel
*Assistant Examiner* — Gwynneth L Howell
(74) *Attorney, Agent, or Firm* — Botos Churchill IP Law LLP

(57) ABSTRACT

Methods and apparatus involve generation of an anti-infection therapy. The method/apparatus may include a controller controlling setting of a respiratory flow therapy device for the therapy. The controller may compute a target flow rate profile for a patient using a margin function, such that the target flow rate profile, according to the margin function, exceeds a minimum inspiratory flow rate profile of the patient's inspiration. The controller may control setting the respiratory flow therapy device to generate a flow of air to a patient interface according to the target flow rate profile, where the generation may be in synchrony with a sensed parameter that is indicative of a breathing cycle of the patient.

34 Claims, 15 Drawing Sheets

(52) U.S. Cl.
 CPC ...... *A61M 16/0069* (2014.02); *A61M 16/101*
  (2014.02); *A61M 16/1055* (2013.01); *A61M*
  *16/107* (2014.02); *A61M 16/109* (2014.02);
  *A61M 2016/0027* (2013.01); *A61M 2016/0039*
  (2013.01); *A61M 2202/0208* (2013.01)

(58) Field of Classification Search
 CPC .......... A61M 16/0003; A61M 16/1055; A61M
  16/107; A61M 16/109; A61M 2016/0039;
  A61M 2016/0027; A61M 2205/3334;
  A61M 2202/0208; A61M 16/021; A61M
  16/024; A61M 16/0051; A61M
  16/0057–0072; A61M 2016/0015–0042
 USPC .................................................... 128/204.23
 See application file for complete search history.

(56) References Cited

U.S. PATENT DOCUMENTS

| | | | |
|---|---|---|---|
| 2009/0065007 A1 | 3/2009 | Wilkinson | |
| 2010/0026367 A1 | 2/2010 | Jiang | |
| 2010/0108066 A1 | 5/2010 | Martin et al. | |
| 2010/0263672 A1 | 10/2010 | Acharya | |
| 2012/0101400 A1* | 4/2012 | Kurosawa | A61B 5/0809 |
| | | | 600/533 |
| 2013/0125892 A1* | 5/2013 | Shelly | A61M 16/0875 |
| | | | 128/204.23 |
| 2016/0022934 A1* | 1/2016 | Soliman | A61M 16/10 |
| | | | 128/204.21 |
| 2016/0045694 A1 | 2/2016 | Esmaeil-Zadeh-Azar | |
| 2016/0193438 A1 | 7/2016 | White et al. | |
| 2018/0036499 A1 | 2/2018 | Kuriger et al. | |

FOREIGN PATENT DOCUMENTS

| | | |
|---|---|---|
| WO | 2013163685 A1 | 11/2013 |
| WO | 2002066105 | 3/2015 |
| WO | 2017072036 A1 | 10/2015 |
| WO | 2015188227 A1 | 12/2015 |
| WO | 2017096428 A1 | 6/2017 |
| WO | 2018090095 A1 | 5/2018 |

OTHER PUBLICATIONS

West, John B, "Respiratory Physiology", Lippincott Williams & Wilkins, 9th edition published 2011.
Supplementary European Search Report for Application No. EP19851330 dated Apr. 22, 2022.
Communication pursuant to Article 94(3) EPC issued in European Patent Application No. 19851330.1, mailed Apr. 4, 2025, 11 pages.

* cited by examiner

Nasal cavity

Oral cavity

Larynx

Vocal folds

Oesophagus

Trachea

Alveolar sacs

Bronchus

Lung

Heart

Diaphragm

METHODS AND APPARATUS FOR CONTROLLING RESPIRATORY THERAPY

1 CROSS-REFERENCE TO RELATED APPLICATIONS

The present application is a national phase entry under 35 U.S.C. § 371 of International Application No. PCT/AU2019/050875 filed Aug. 20, 2019, published in English, which claims priority from Australian Provisional Patent Application No. 2018903109, filed Aug. 23, 2018, all of which are incorporated herein by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use. More particularly, present technology concerns methods and apparatus for controlling a respiratory flow therapy device to provide an anti-infection therapy.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, ninth edition, published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapies

Various respiratory therapies, such as Continuous Positive Airway Pressure (CPAP) therapy, Non-invasive ventilation (NIV), Invasive ventilation (IV), and high flow therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open interface at controlled flow rates similar to, or greater than peak inspiratory flow rate. HFT has been used to treat OSA, CSR, COPD and other respiratory disorders.

One mechanism of action is that the high flow rate of air at the airway entrance improves ventilation efficiency by flushing, or washing out, expired $CO_2$ from the patient's anatomical deadspace. HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

Another form of flow therapy is long-term oxygen therapy (LTOT). Doctors may prescribe a continuous flow of oxygen-enriched air at a specified purity (from 21%, the oxygen fraction in ambient air, to 100%) at a specified flow rate (e.g., 1 litre per minute (LPM), 2 LPM, 3 LPM, etc.) to be delivered to the patient's airway.

2.2.2.3 Supplementary Oxygen

For certain patients, oxygen therapy may be combined with a respiratory pressure therapy or HFT by adding supplementary oxygen to the pressurised flow of air. When oxygen is added to respiratory pressure therapy, this is referred to as RPT with supplementary oxygen. When oxygen is added to HFT, the resulting therapy is referred to as HFT with supplementary oxygen, or high flow oxygen therapy (HFOT).

2.2.3 Respiratory Therapy Systems

These respiratory therapies may be provided by a respiratory therapy system or device. A respiratory therapy system may comprise a Respiratory Therapy Device (RT device), a patient interface, an air circuit, a humidifier, and an oxygen source.

2.2.3.1 Respiratory Therapy (RT) Device

A respiratory therapy (RT) device is configured to generate a flow of air for delivery to an interface to the airways. The flow of air may be pressure-controlled (for respiratory pressure therapies) or flow-controlled (for flow therapies such as HFT). Thus, RT devices may act as respiratory pressure therapy (RPT) devices and/or respiratory flow therapy devices. Examples of RPT devices include CPAP devices and ventilators.

2.2.3.2 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. For pressure therapies, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For flow therapies such as nasal HFT, the patient interface may be configured to insufflate the nares but specifically to avoid a complete seal. One example of such an unsealed patient interface is a nasal cannula.

2.2.3.3 Air Circuit

An air circuit is a conduit or a tube constructed and arranged to allow, in use, a flow of air to travel between two components of a therapy system such as the RPT device and the patient interface. In some cases, there may be separate limbs of the air circuit for inhalation and exhalation. In other cases, a single limb air circuit is used.

2.2.3.4 Humidifier

Delivery of a flow of air without humidification may cause drying of the airways. The use of a humidifier with an RPT device produces humidified air that minimizes drying of the nasal mucosa and increases patient airway comfort. In addition, in cooler climates, warm air applied generally to the face area in and about the patient interface is more comfortable than cold air. Humidifiers therefore often have the capacity to heat the flow of air as well as humidifying it.

2.2.3.5 Oxygen Source

Experts in this field have recognized that exercise for respiratory failure patients provides long term benefits that slow the progression of the disease, improve quality of life and extend patient longevity. Most stationary forms of exercise like tread mills and stationary bicycles, however, are too strenuous for these patients. As a result, the need for mobility has long been recognized. Until recently, this mobility has been facilitated by the use of small compressed oxygen tanks or cylinders mounted on a cart with dolly wheels. The disadvantage of these tanks is that they contain a finite amount of oxygen and are heavy, weighing about 50 pounds when mounted.

Oxygen concentrators have been in use for about 50 years to supply oxygen for respiratory therapy. Traditional oxygen concentrators have been bulky and heavy making ordinary ambulatory activities with them difficult and impractical. Recently, companies that manufactured large stationary oxygen concentrators began developing portable oxygen concentrators (POCs). The advantage of POCs is that they can produce a theoretically endless supply of oxygen. In order to make these devices small for mobility, the various systems necessary for the production of oxygen enriched gas are condensed. POCs seek to utilize their produced oxygen as efficiently as possible, in order to minimise weight, size, and power consumption. This may be achieved by delivering the oxygen as series of pulses or "boli", each bolus timed to coincide with the start of inspiration. This therapy mode is known as pulsed or demand (oxygen) delivery (POD), in contrast with traditional continuous flow delivery more suited to stationary oxygen concentrators.

For sufferers of advanced COPD (and also other chronic diseases such as congestive heart failure) the risk of respiratory infection is amplified, as it may lead to mortality or irreversible increase in morbidity. Furthermore, many sufferers of respiratory disease are more vulnerable to respiratory infection from other people, ambient irritants, and extreme cold. Such people may routinely avoid social exposure, public transport, etc. as a result, which in turn leads to isolation and anxiety.

A breathing mask is commonly used to prevent infection from ambient pollution/particulates, however there may be situations where a mask is problematic, such as while speaking, while eating, in hot climates, and if culturally unacceptable (e.g. perception of contagion from the wearer).

3 BRIEF SUMMARY OF THE TECHNOLOGY

The present technology is directed towards providing medical devices used in the amelioration or prevention of respiratory disorders having one or more of improved comfort, cost, efficacy, ease of use and manufacturability.

One form of the present technology comprises a portable device configured to deliver filtered air via a minimal unsealed nasal interface during inspiration, at a flow rate sufficient to meet or just exceed the wearer's inspiratory flow rate, and thus prevent entrainment of ambient air during inspiration. In doing so, the risk of infection from nasal inhalation of ambient pathogens is greatly diminished. By delivering air only during the inspiratory phase, and then only just above the patient's inspiratory demand, power consumption is reduced compared to conventional high flow therapy, as is any drying effect on the nares from the gas flow.

Further optional features are (a) to humidify the delivered air to further reduce the drying effects of the gas flow, and/or (b) to enrich the air with oxygen from a portable oxygen source, such as a portable oxygen concentrator (POC) or oxygen cylinder configured with a conserver to operate in POD mode. In the case of a patient who requires long-term oxygen therapy via nasal cannula, the disclosed device may offer additional infection- or pollution-minimization benefits on top of their existing therapy.

Some versions of the present technology may include a method of a controller controlling setting of a respiratory flow therapy device for an anti-infection therapy. The method may include computing, by the controller of the respiratory flow therapy device, a target flow rate profile for a patient using a margin function, such that the target flow rate profile exceeds, according to the margin function, a minimum inspiratory flow rate profile of the patient's inspiration. The method may include controlling setting of the respiratory flow therapy device to generate a flow of air with the respiratory flow therapy device according to the target flow rate profile, wherein the generation may be in synchrony with a sensed parameter that may be indicative of a breathing cycle of the patient.

In some versions, the margin function may be configured such that the target flow rate profile marginally exceeds the minimum inspiratory flow rate profile of the patient. The computing may include computing the minimum inspiratory flow rate profile of the patient. Computing the target flow rate profile during inspiration may include adding the margin function to the minimum inspiratory flow rate profile. The margin function may be a function of a peak inspiratory flow rate. The method may further include estimating the peak inspiratory flow rate. The function of the peak inspiratory flow rate may include a percentage. The percentage may be in a range of 10 to 30 percent. The margin function may include a multiple of the minimum inspiratory flow rate profile. The multiple may be in a range of 0.1 to 0.3.

In some versions, computing the minimum inspiratory flow rate profile may include estimating a peak inspiratory flow rate of the patient based on the patient's height. Computing the minimum inspiratory flow rate profile may include computing the minimum inspiratory flow rate profile from the peak inspiratory flow rate. Estimating the peak inspiratory flow rate may include computing an estimate of anatomic deadspace, computing an estimate of minimum ventilation, and computing an estimate of minimum tidal volume. Computing the target flow rate profile during expiration may include setting the target flow rate profile to zero.

The method may also include computing a new target flow rate profile for the patient, and controlling setting of the respiratory flow therapy device to further generate a flow of air with the respiratory flow therapy device according to the new target flow rate profile. The further generation may be in synchrony with a sensed parameter that may be indicative of a subsequent breathing cycle of the patient. Computing the new target flow rate profile may include estimating at least one value of nasal pressure of the patient over an inspiratory portion of a breathing cycle of the patient, and computing a new target flow rate profile based on the at least one nasal pressure value. Estimating at least one value of nasal pressure of the patient over an inspiratory portion of the patient's breathing cycle may include receiving a measure of pressure and adjusting the measure of pressure according to a characteristic function of an air circuit of the respiratory flow therapy device through which the pressure may be measured. The characteristic function may include a measured flow value and a pressure drop value. Computing the new target flow rate profile may include controlling adjustment to a peak inspiratory flow rate based on the at least one nasal pressure value, computing a new minimum inspiratory flow rate profile of the patient from the adjusted peak inspiratory flow rate, and computing the new target flow rate profile using the margin function. Controlling adjustment to the peak inspiratory flow rate may include (a) decreasing the peak inspiratory flow rate if the at least one nasal pressure value may be above a threshold target; and/or (b) increasing the peak inspiratory flow rate if the at least one nasal pressure value may be below a threshold target.

In some versions, computing the target flow rate profile may include receiving estimated breath timing parameters. The estimated breath timing parameters may include an estimated breathing rate and/or an estimated inspiratory time. The method may further include computing the estimated breath timing parameters by computing impedance or conductance from pressure and flow signals. The method may include generating a dynamic impedance signal or dynamic conductance signal with the computed impedance or conductance respectively. The method may include determining trigger and/or cycling points from the dynamic impedance signal or the dynamic conductance signal. The method may include controlling an oxygen source to add supplementary oxygen to the generated flow of air. The supplementary oxygen may be added in pulsed oxygen delivery (POD) mode. The method may include conditioning, by a humidifier of the respiratory flow therapy device, the generated flow of air.

Some versions of the present technology may include a processor-readable medium, having stored thereon processor-executable instructions which, when executed by a processor of a controller, cause the controller to control setting of a respiratory flow therapy device for an anti-infection therapy according to any of the methods described herein.

Some versions of the present technology may include an anti-infection therapy device. The anti-infection therapy device may include a pressure generator configured to generate a flow of air at a controllable flow rate to a patient interface. The anti-infection therapy device may include a controller that may include one or more processors and a memory. The one or more processors may be configured to execute program instructions stored in the memory. The program instructions may be configured to perform any one or more of the aspects of the methods described herein.

Some versions of the present technology may include an anti-infection therapy device. The anti-infection therapy device may include a pressure generator configured to generate a flow of air at a controllable flow rate to a patient interface. The anti-infection therapy device may include a controller. The controller may be configured to compute a target flow rate profile for a patient using a margin function, such that the target flow rate profile exceeds, according to the margin function, a minimum inspiratory flow rate profile of the patient's inspiration. The controller may be configured to control setting of the pressure generator to generate a flow of air to the patient interface according to the target flow rate profile, wherein the generation may be in synchrony with a sensed parameter that may be indicative of a breathing cycle of the patient.

The anti-infection therapy device may include an oxygen source configured to add supplementary oxygen to the generated flow of air. The oxygen source may be configured to add the supplementary oxygen in pulsed oxygen delivery (POD) mode. The anti-infection therapy device may include a humidifier configured to condition the generated flow of air.

Some versions of the present technology may include an anti-infection therapy device. The anti-infection therapy device may include means for generating a flow of air at a controllable flow rate to a patient interface. The anti-infection therapy device may include means for computing a target flow rate profile for a patient using a margin function, such that the target flow rate profile exceeds, according to the margin function, a minimum inspiratory flow rate profile of the patient's inspiration. The anti-infection therapy device may include means for controlling the means for generating to generate the flow of air according to the target flow rate profile, wherein the generation may be in synchrony with a sensed parameter that may be indicative of a breathing cycle of the patient.

In accordance with one aspect of the present technology, there is disclosed a method of delivering anti-infection therapy to a patient. The method comprises computing, by a controller of a respiratory flow therapy device, a target flow rate profile for the patient, such that the target flow rate profile slightly exceeds a minimum inspiratory flow rate profile of the patient during inspiration; and controlling the respiratory flow therapy device to deliver of a flow of air to the airway of the patient according to the target flow rate profile in synchrony with the breathing cycle of the patient.

In accordance with another aspect of the present technology, there is disclosed an anti-infection therapy device. The device comprises: a pressure generator configured to deliver a flow of air at a controllable flow rate to an airway of a patient; and a controller configured to: compute a target flow rate profile for the patient, such that the target flow rate profile slightly exceeds a minimum inspiratory flow rate profile of the patient during inspiration; and control the pressure generator to deliver of a flow of air to the patient's airway according to the target flow rate profile in synchrony with the breathing cycle of the patient.

In accordance with still another aspect of the present technology, there is disclosed anti-infection therapy apparatus comprising: means for delivering a flow of air at a controllable flow rate to an airway of a patient; means for computing a target flow rate profile for the patient, such that the target flow rate profile slightly exceeds a minimum inspiratory flow rate profile of the patient during inspiration; and means for controlling the means for delivering to deliver a flow of air to the patient's airway according to the target flow rate profile in synchrony with the breathing cycle of the patient.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1 shows a system including a patient 1000 wearing a patient interface 3000, in the form of a full-face mask, receiving a supply of air at positive pressure from an RPT device 4000. Air from the RPT device is conditioned in a humidifier 5000, and passes along an air circuit 4170 to the patient 1000.

4.2 Respiratory System

FIG. 2 shows an overview of a human respiratory system including the nasal and oral cavities, the larynx, vocal folds, oesophagus, trachea, bronchus, lung, alveolar sacs, heart and diaphragm.

4.3 Patient Interface

FIG. 3 shows a patient 1000 wearing an example of an unsealed patient interface 3800 in the form of a nasal cannula in accordance with one form of the present technology. The patient interface 3800 may be fluidly coupled to receive breathable gas from an RPT device and/or a POC device so as to provide a flow therapy, such as an anti-infection therapy as described in more detail herein.

4.4 RPT Device

FIG. 4A shows an RPT device in accordance with one form of the present technology.

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

FIG. 4C is a schematic diagram of the electrical components of an RPT device in accordance with one form of the present technology.

4.5 Humidifier

4.6 Breathing Waveforms

Figure 6:
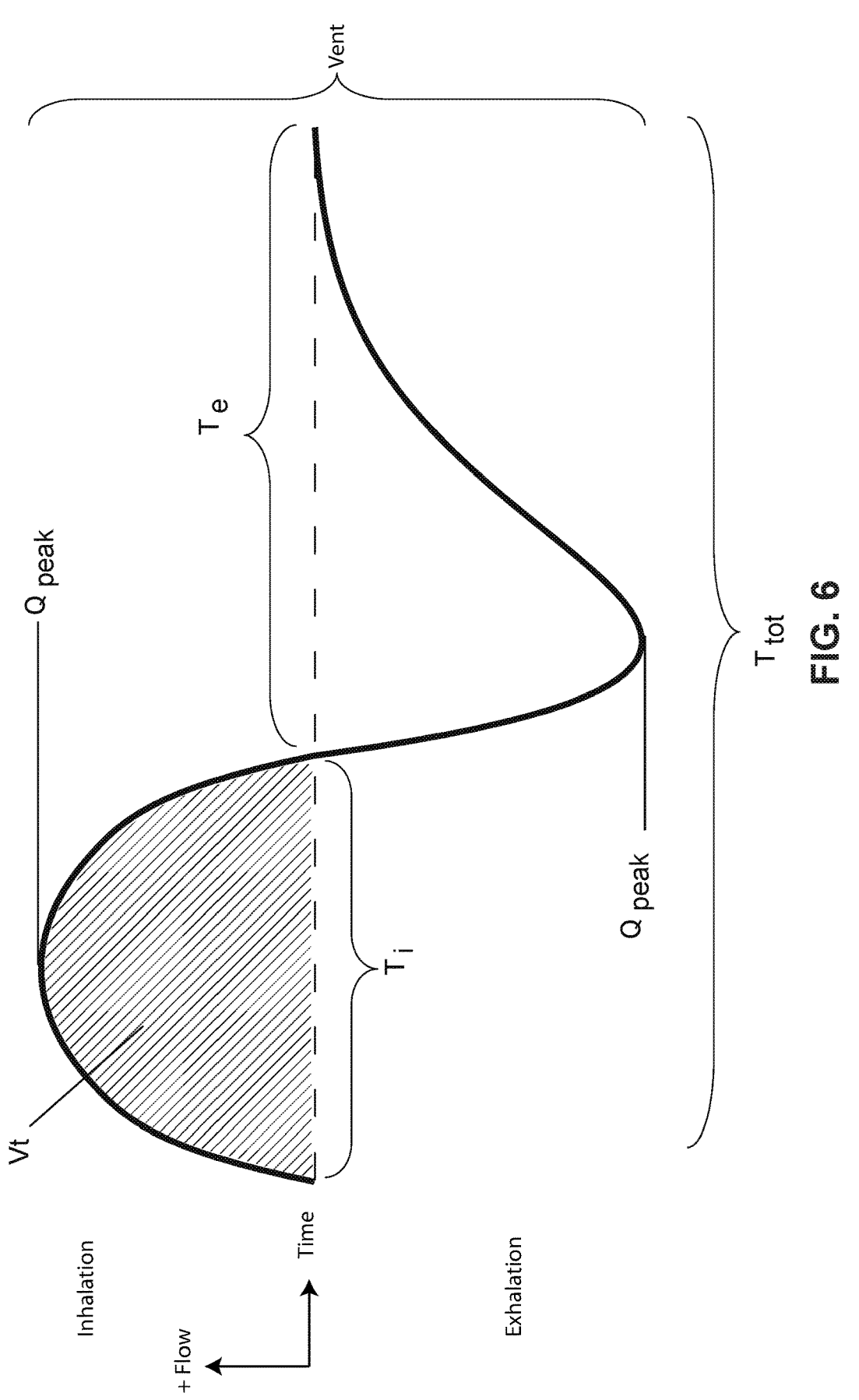

FIG. 6 shows a model typical respiratory flow rate waveform of a person while sleeping. The horizontal axis is time, and the vertical axis is respiratory flow rate. While the parameter values may vary, a typical breath of a healthy adult may have the following approximate values: tidal volume Vt 0.5 L, inspiratory time $T_I$ 1.6 s, peak inspiratory flow rate Qpeak 0.4 L/s, expiratory time Te 2.4 s, peak expiratory flow rate Qpeak–0.5 L/s. The total time, Ttot, is about 4 s. The person's breathing rate Rb is about 15 breaths per minute (BPM), with ventilation about 7.5 L/min. The patient's duty cycle, the ratio of Ti to Ttot, is about 40%.

4.7 Oxygen Concentrator

Figure 7A:
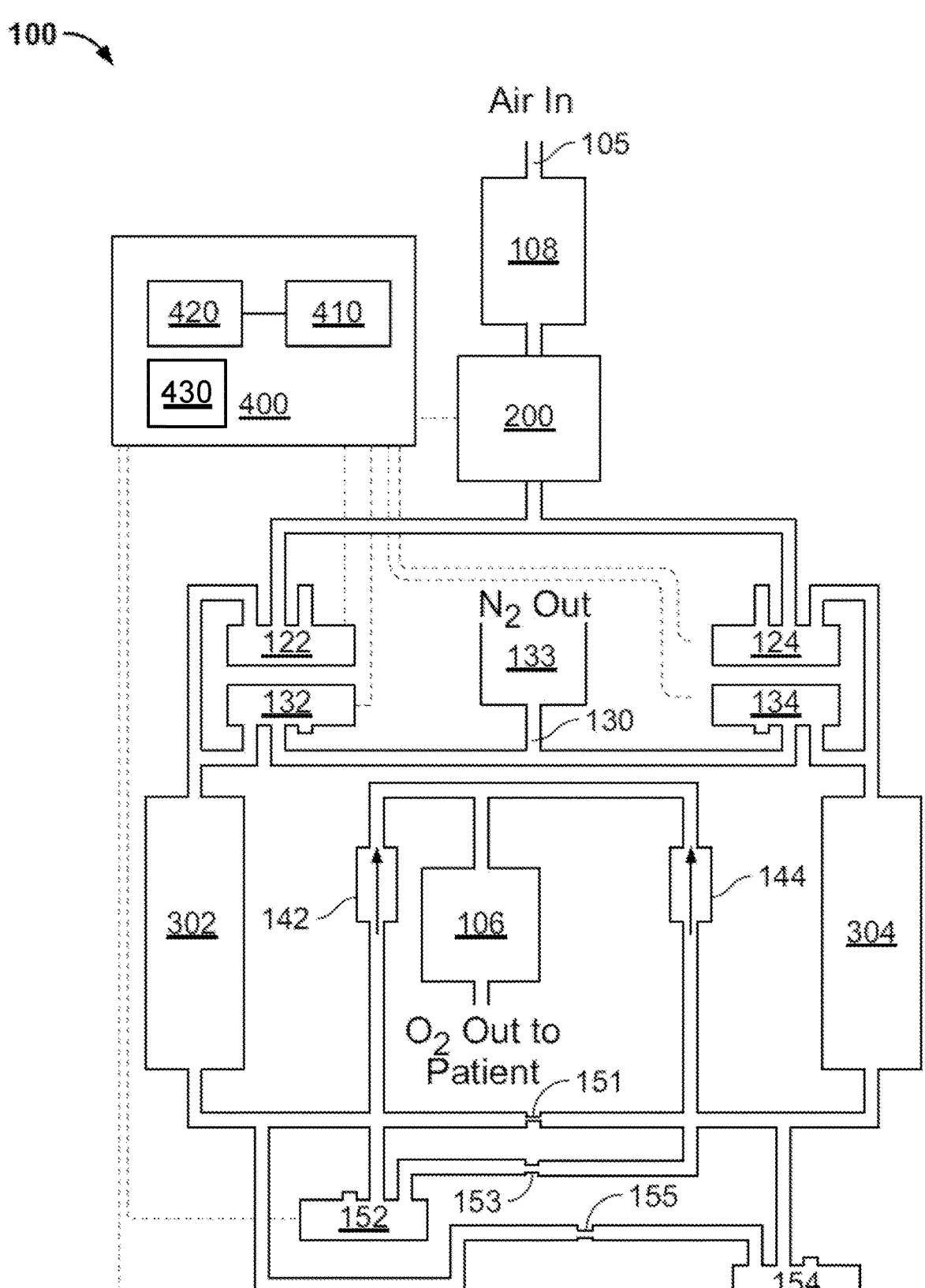

FIG. 7A is a schematic diagram of the components of an oxygen concentrator according to one form of the present technology.

Figure 7B:
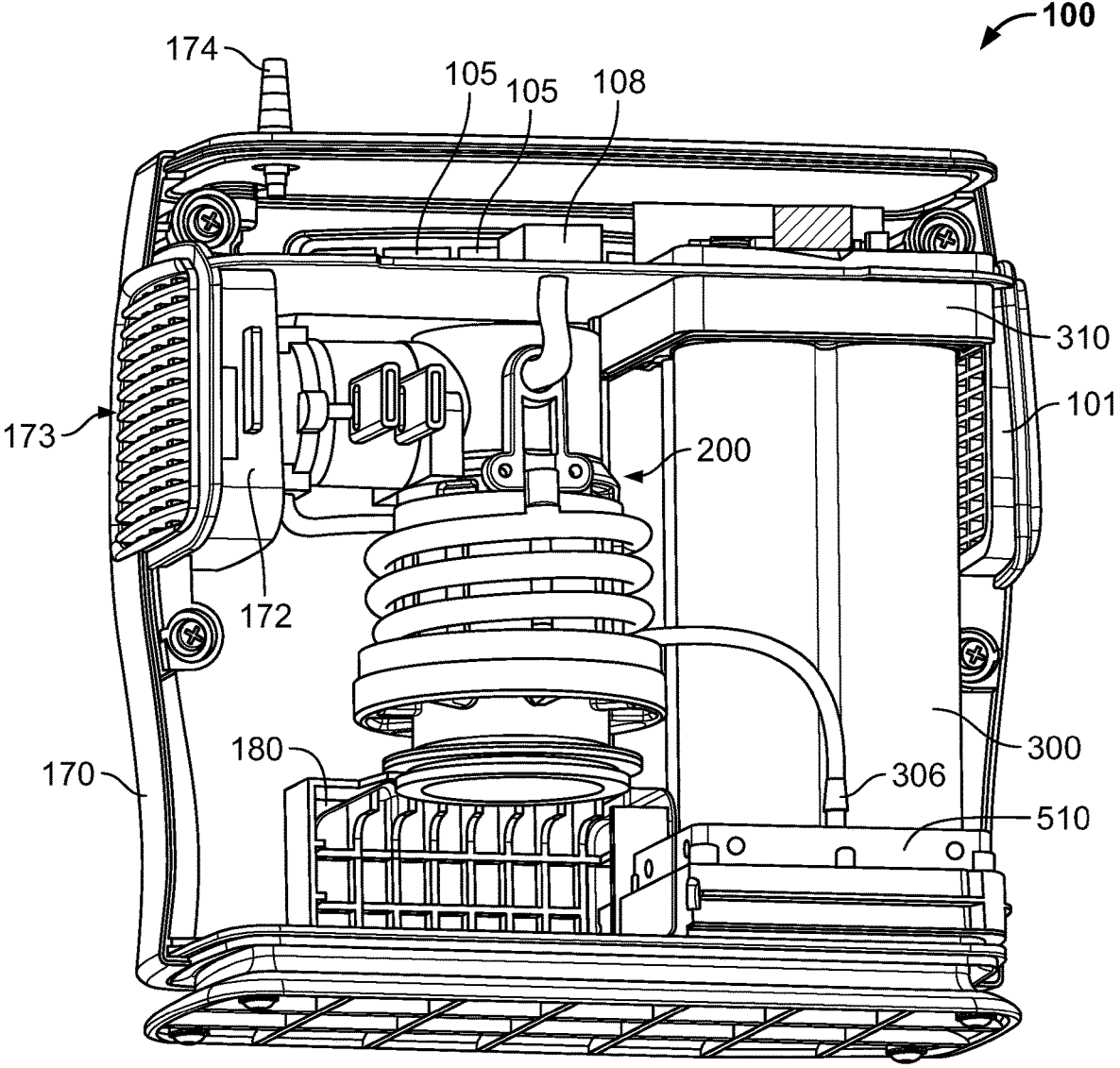

FIG. 7B is a side view of the main components of the oxygen concentrator of FIG. 7A.

Figure 7C:
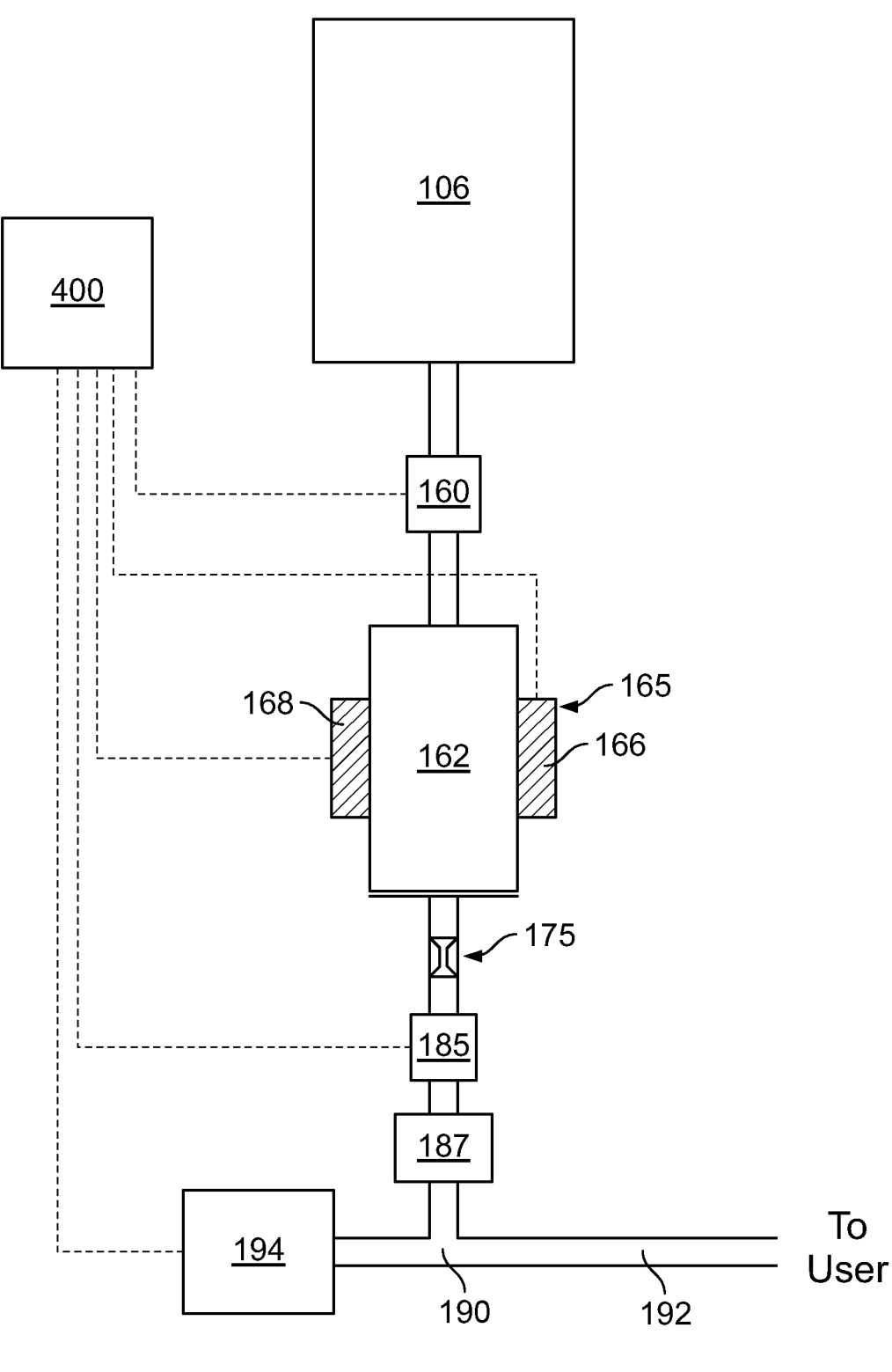

FIG. 7C is a schematic diagram of the outlet system of the oxygen concentrator of FIG. 7A.

Figure 7D:
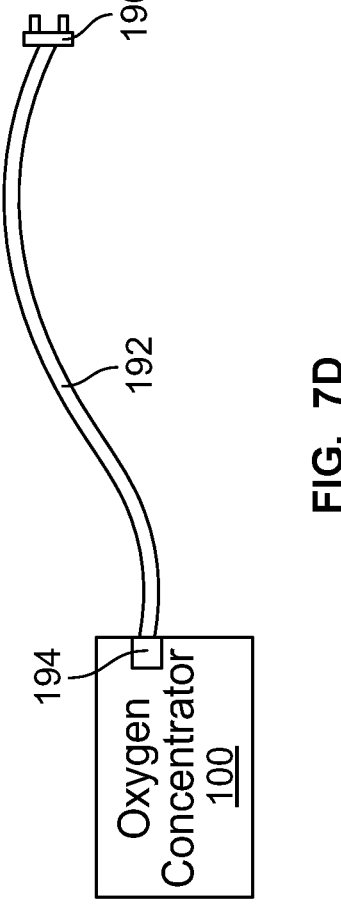

FIG. 7D depicts an outlet conduit and interface for the oxygen concentrator of FIG. 7A.

4.8 Anti-Infection Therapy

Figure 8:
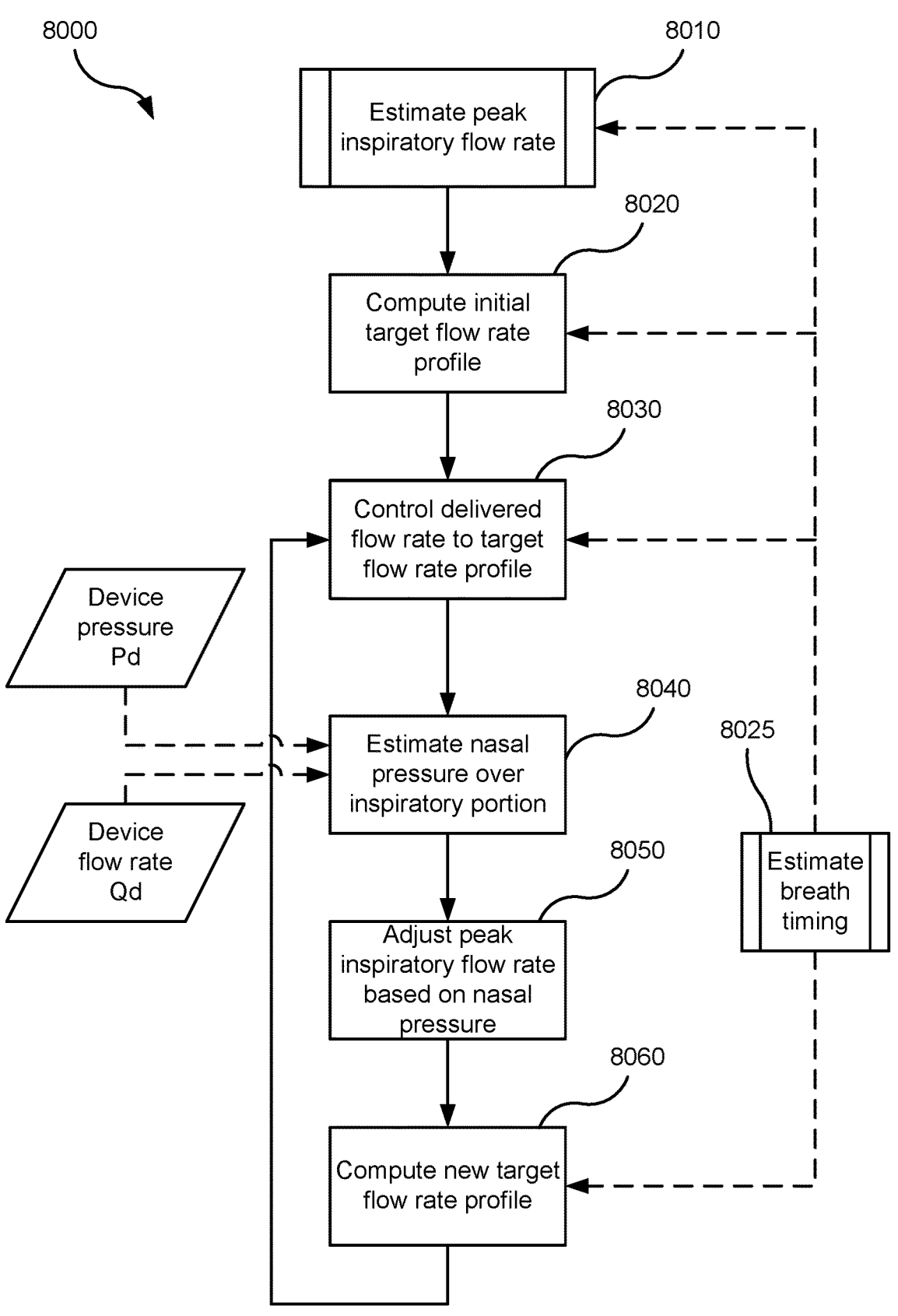

FIG. 8 is a flow chart illustrating a method of implementing an anti-infection therapy, such as with a controller (e.g., central processor) of the devices described herein, according to one form of the present technology.

Figure 9:
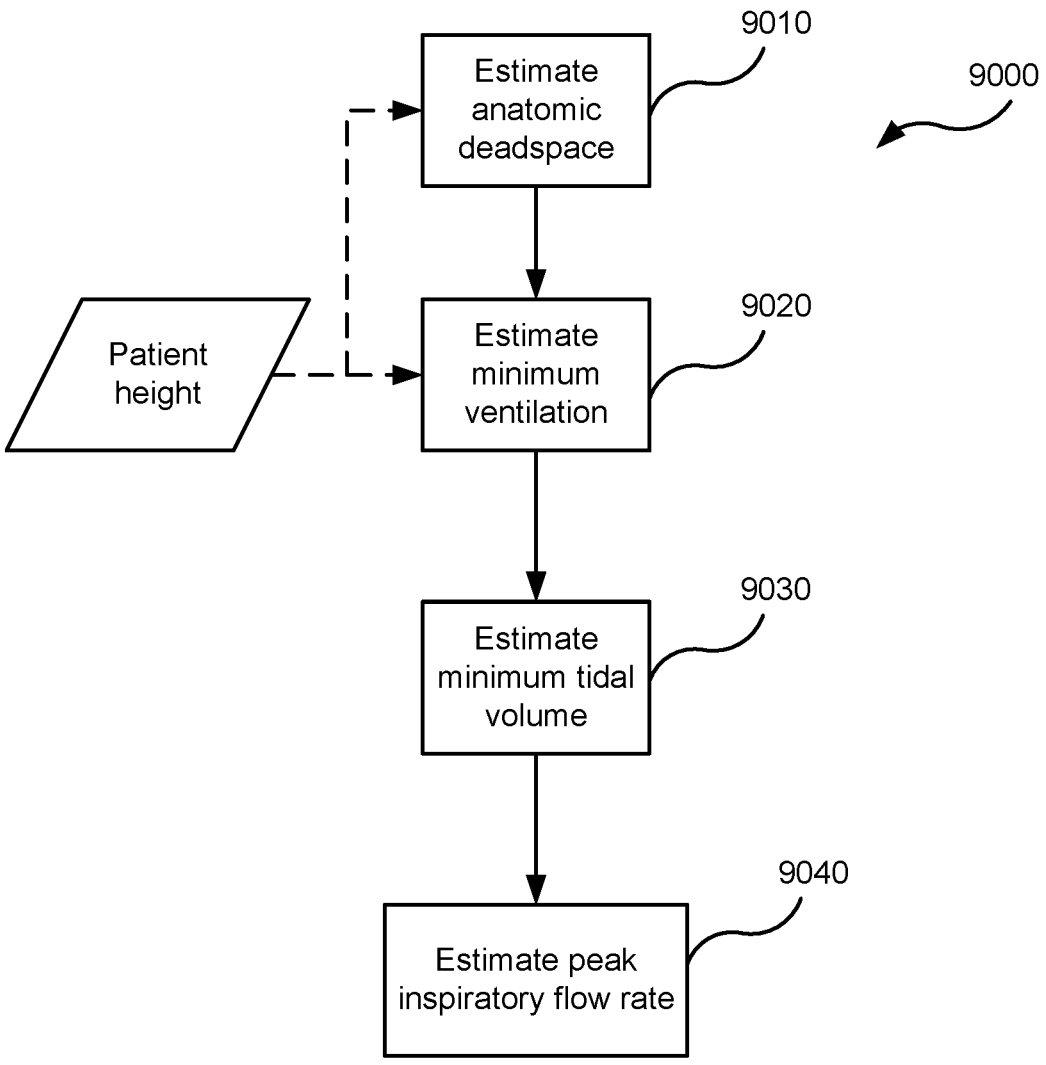

FIG. 9 is a flow chart illustrating a method of estimating a peak inspiratory flow rate such as for use in the method of FIG. 8 in one form of the present technology.

Figure 10:
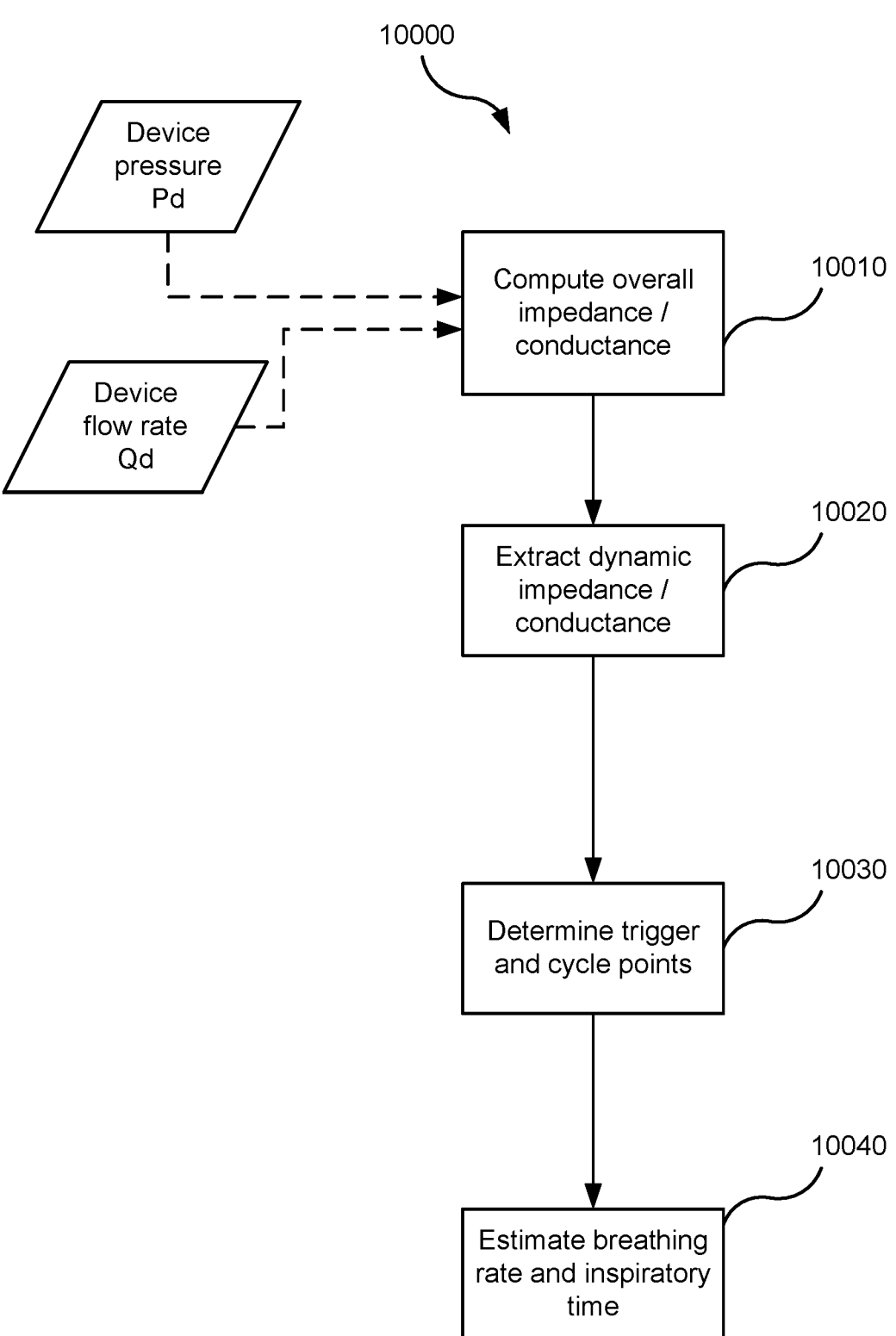

FIG. 10 is a flow chart illustrating a method of estimating breath timing such as for use in the method of FIG. 8 in one form of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Respiratory Therapy Systems

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3800.

5.1.1 Patient Interface

Figure 1:
Figure 2:
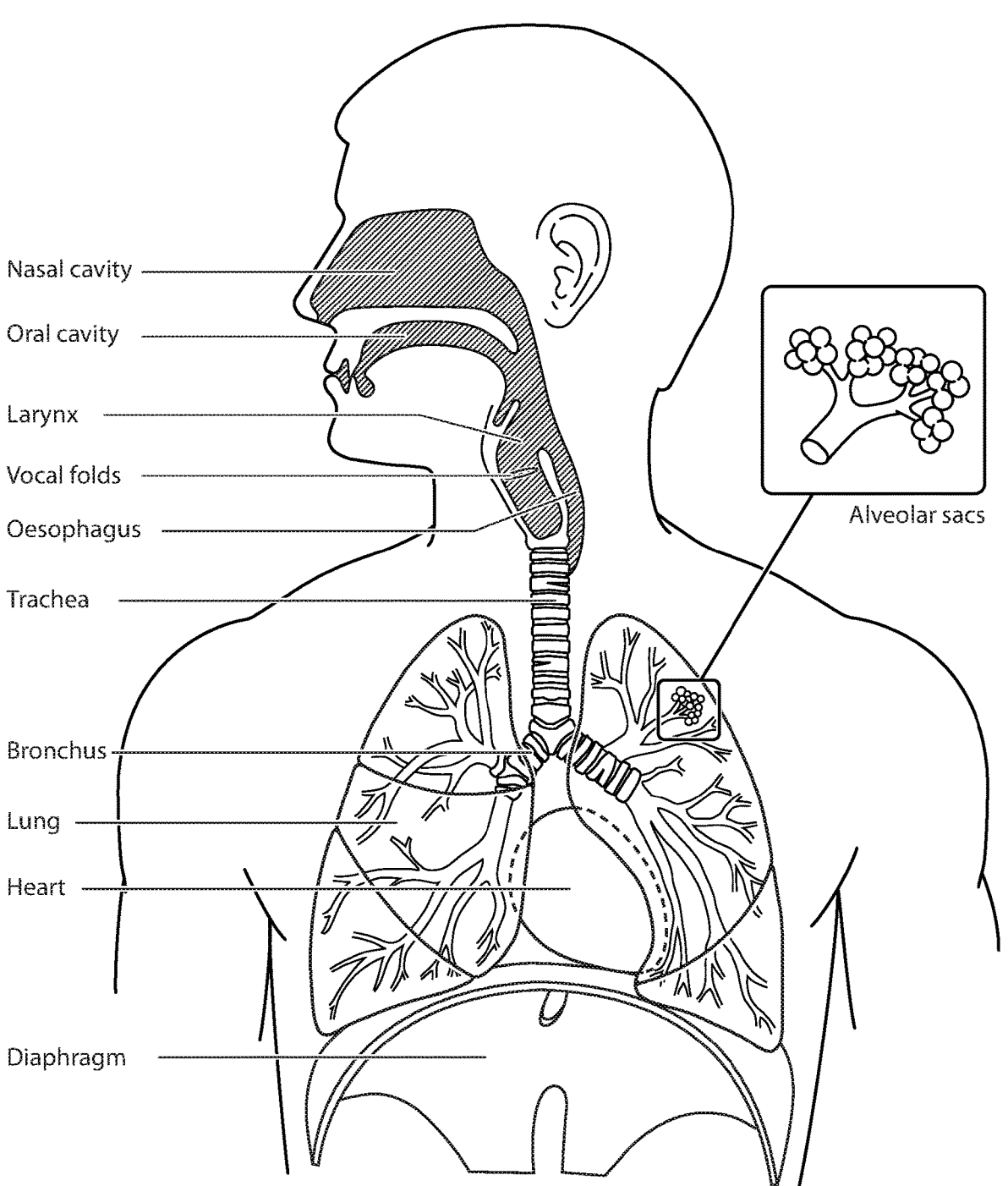
Figure 3:
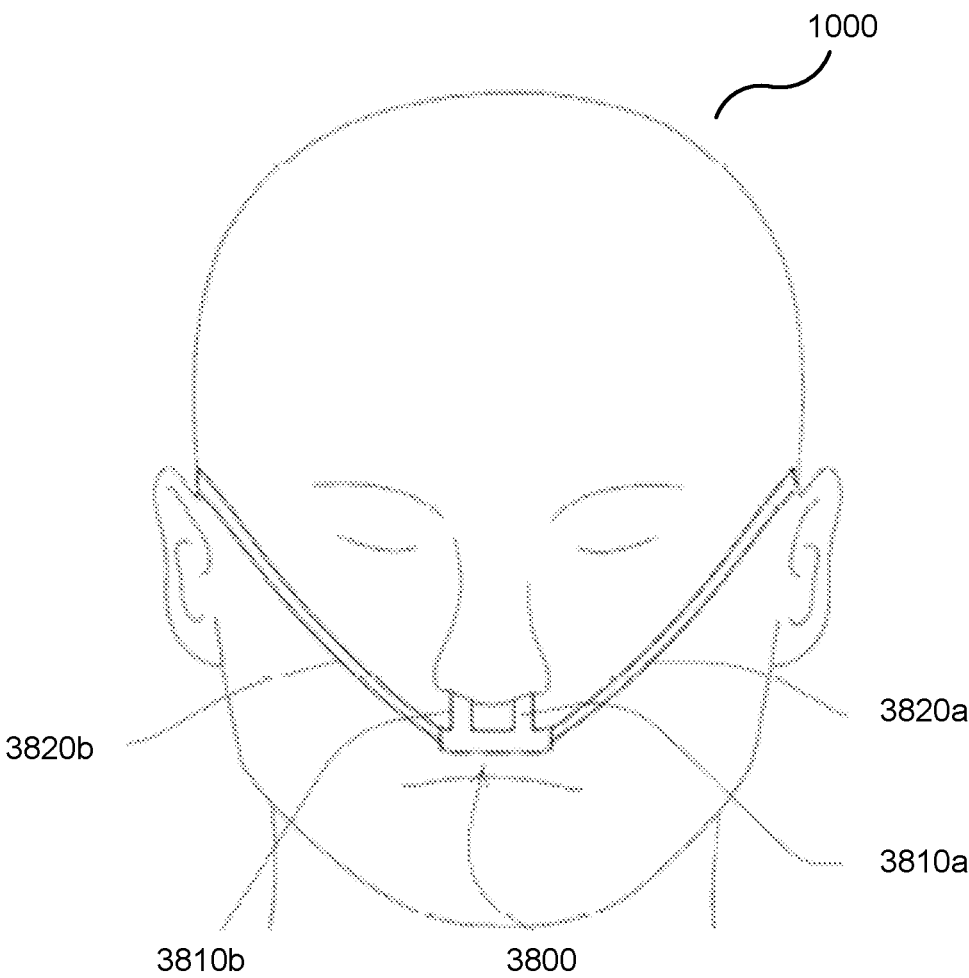
Figure 4A:
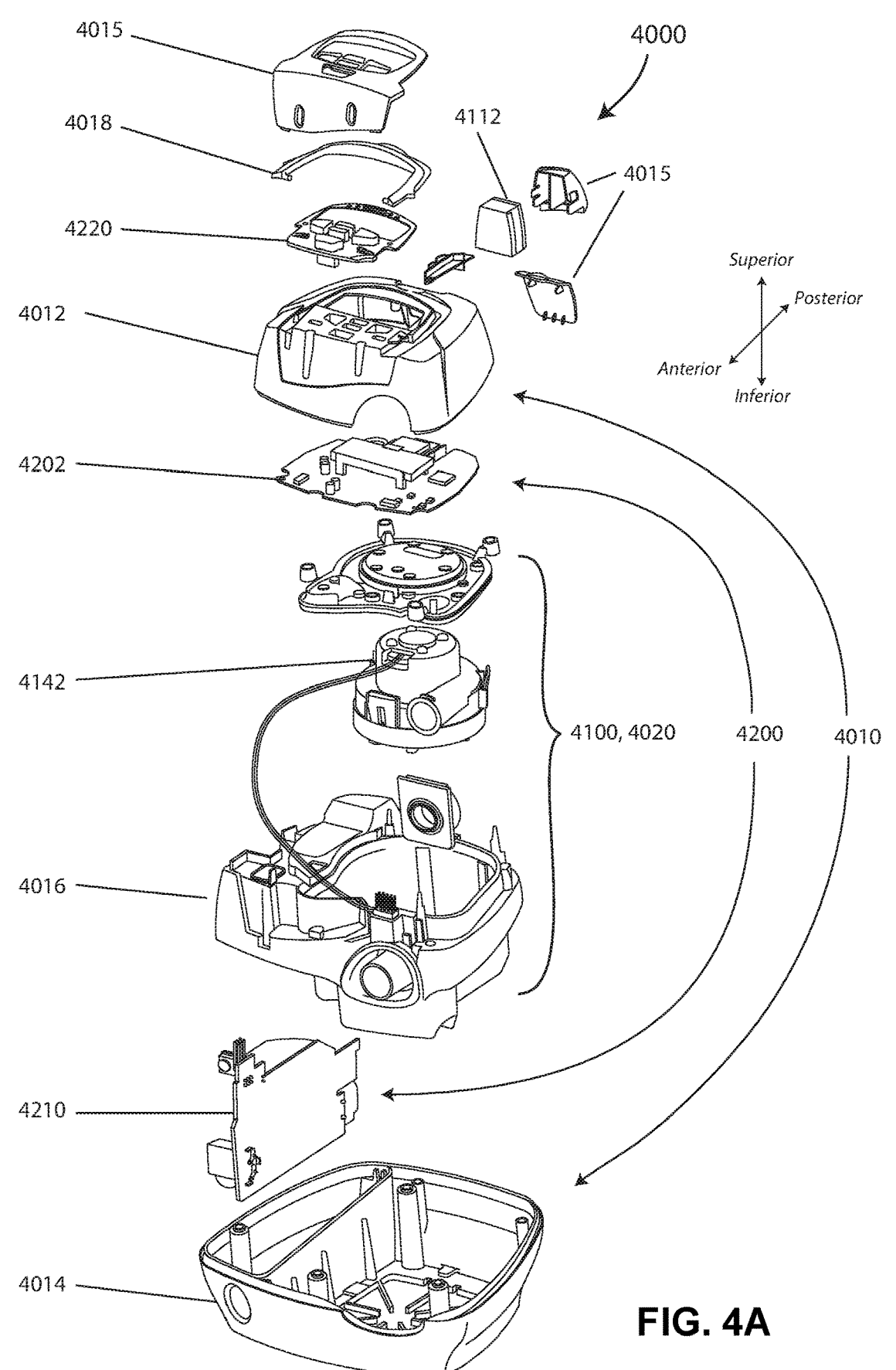
Figure 4B:
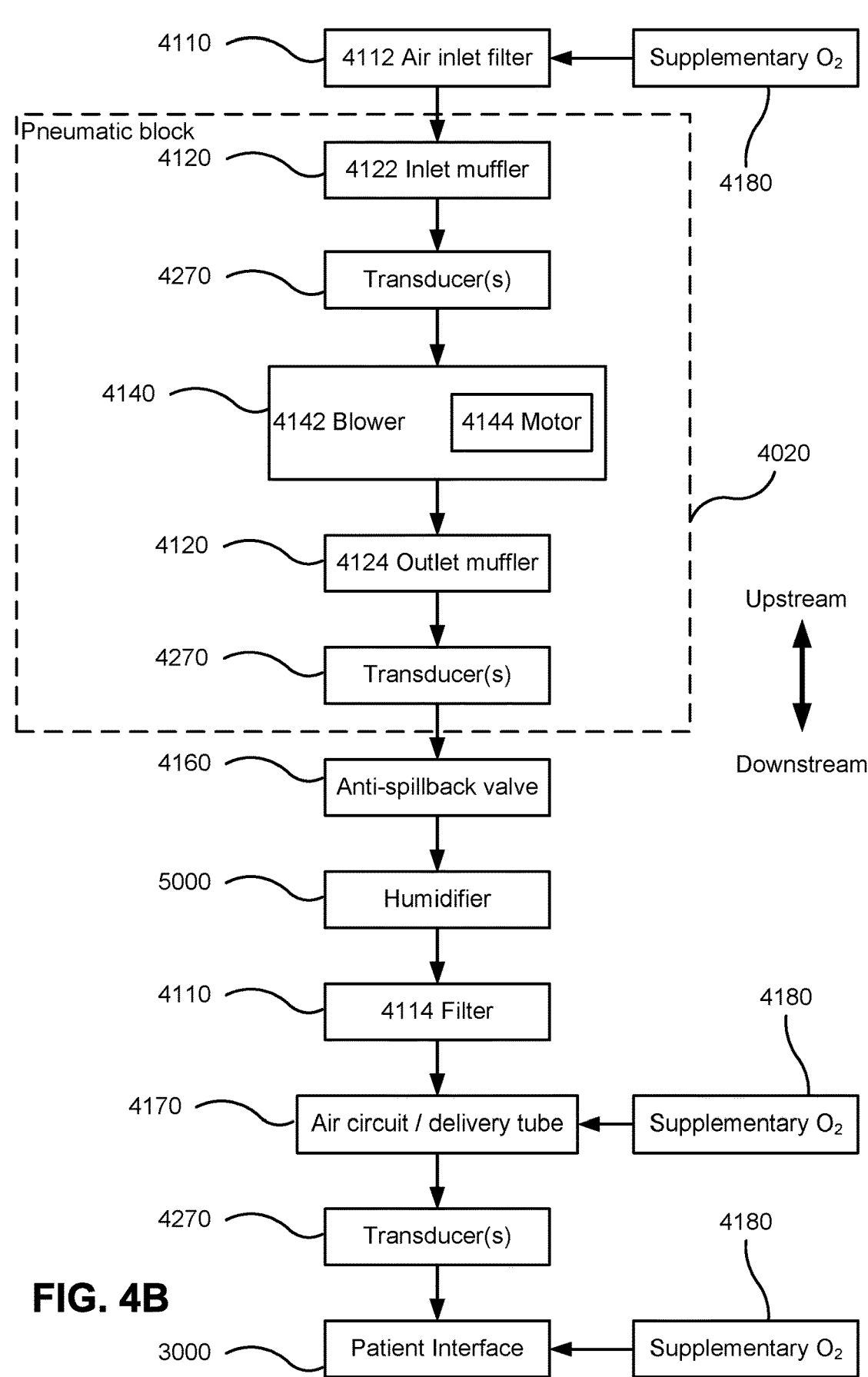
Figure 4C:
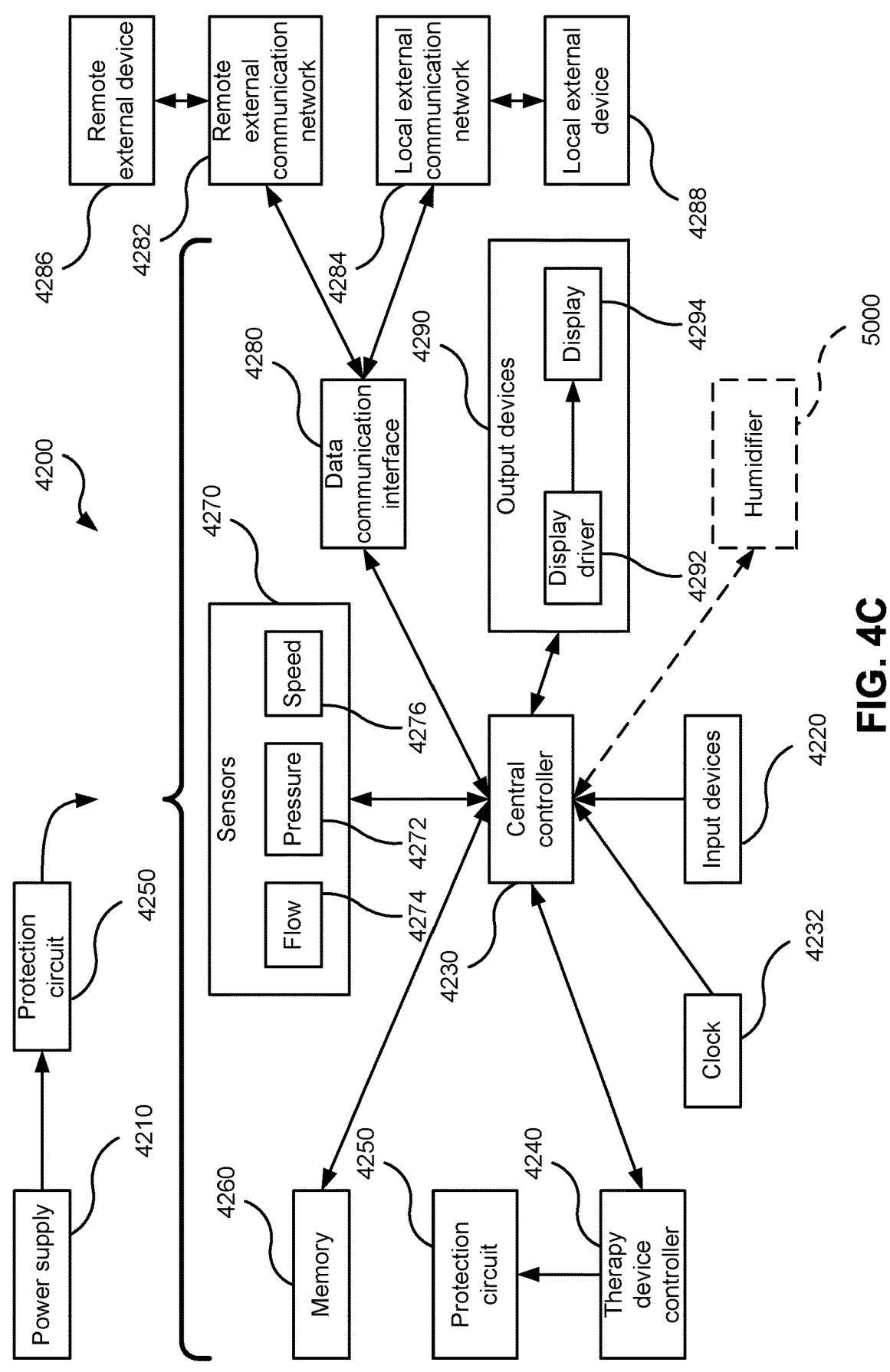

An unsealed patient interface 3800, which may be in the form of a nasal cannula, such as one illustrated in FIG. 3, includes nasal prongs 3810*a*, 3810*b* which can deliver air to respective nares of the patient 1000 via respective orifices in their tips. Such nasal prongs do not generally form a seal with the inner or outer skin surface of the nares. The air to the nasal prongs may be delivered by one or more air supply lumens 3820*a*, 3820*b* that are coupled with the nasal cannula-type unsealed patient interface 3800. The lumens 3820*a*, 3820*b* lead from the nasal cannula-type unsealed patient interface 3800 to a respiratory therapy device via an air circuit. The unsealed patient interface 3800 is particularly suitable for delivery of flow therapies, in which the RPT device generates the flow of air at controlled flow rates rather than controlled pressures. The "vent" at the unsealed patient interface 3800, through which excess airflow escapes to ambient, is the passage between the end of the prongs 3810*a* and 3810*b* of the nasal cannula-type unsealed patient interface 3800 via the patient's nares to atmosphere.

5.1.2 Air Circuit

An air circuit 4170 in accordance with one form of the present technology is a conduit or a tube constructed and arranged to allow, in use, a flow of air to travel between two components such as RPT device 4000 and the patient interface 3800.

In particular, the air circuit 4170 may be in fluid connection with the outlet of the pneumatic block 4020 and the patient interface 3800. In some forms, there may be separate limbs of the circuit for inhalation and exhalation. In other forms, a single limb circuit is used.

5.1.3 RPT Device

An RPT device 4000 comprises mechanical, pneumatic, and/or electrical components and is configured to execute one or more algorithms, such as any of the methods, in whole or in part, described herein. The RPT device 4000 may be configured to generate a flow of air for delivery to a patient's airways, such as to treat one or more of the respiratory conditions described elsewhere in the present document.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of delivering a flow of air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.1.3.1 RPT Device Mechanical & Pneumatic Components

An RPT device may comprise one or more of the following components in an integral unit. In an alternative form, one or more of the following components may be located as respective separate units.

5.1.3.1.1 Air Filter(s)

An RPT device in accordance with one form of the present technology may include an air filter 4110, or a plurality of air filters 4110.

In one form, an inlet air filter 4112, for example an antibacterial filter, is located at the beginning of the pneumatic path upstream of a pressure generator 4140.

In one form, in addition or alternatively to the inlet air filter 4112, an outlet air filter 4114, for example an antibacterial filter, is located between an outlet of the pneumatic block 4020 and a patient interface 3800.

5.1.3.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3800.

5.1.3.1.3 Pressure Generator

In one form of the present technology, a pressure generator 4140 for producing a flow, or a supply, of air at positive pressure is a controllable blower 4142. For example, the blower 4142 may include a brushless DC motor 4144 with one or more impellers housed in a blower housing, such as in a volute. The blower 4142 may be capable of delivering a supply of air at a controllable flow rate, for example at a rate of up to about 70 to 80 litres per minute. The blower may be as described in any one of the following patents or patent applications the contents of which are incorporated herein by reference in their entirety: U.S. Pat. Nos. 7,866, 944; 8,638,014; 8,636,479; and PCT Patent Application Publication No. WO 2013/020167.

The pressure generator 4140 may be under the control of the therapy device controller 4240.

In other forms, a pressure generator 4140 may be a piston-driven pump, a pressure regulator connected to a high pressure source (e.g. compressed air reservoir), or a bellows.

5.1.3.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form, a signal from a transducer 4270 may be filtered, such as by low-pass, high-pass or band-pass filtering.

5.1.3.1.4.1 Flow Rate Sensor

A flow rate sensor 4274 in accordance with the present technology may be based on a differential pressure transducer, for example, an SDP600 Series differential pressure transducer from SENSIRION.

In one form, a signal representing a flow rate of the flow of air at the output of the RPT device 4000 (the device flow rate Qd) is generated by the flow rate sensor 4274.

5.1.3.1.4.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal representing a pressure of the flow of air at the output of the RPT device 4000 (the device pressure Pd) is generated by the pressure sensor 4272.

5.1.3.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

5.1.3.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.1.3.1.6 Supplementary Gas Delivery

In one form of the present technology, supplementary gas, e.g. oxygen 4180 is delivered to one or more points in the pneumatic path, such as upstream of the pneumatic block 4020, to a point in the air circuit 4170, and/or at the patient interface 3800.

5.1.3.2 RPT Device Electrical Components

5.1.3.2.1 Power Supply

A power supply 4210 may be located internal or external to the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.1.3.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.1.3.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELEC-TRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to execute the one or more methodologies described herein, such as the one or more algorithms which may be implemented with processor-control instructions, expressed as computer programs stored in a non-transitory computer readable storage medium, such as memory 4260. In some forms of the present technology, the central controller 4230 may be integrated with the RPT device 4000.

5.1.3.2.4 Clock

The RPT device 4000 may include a clock 4232 that is connected to the central controller 4230.

5.1.3.2.5 Therapy Device Controller

In one form of the present technology, therapy device controller 4240 is a therapy control module 4330 that forms part of the algorithms executed by the central controller 4230.

In one form of the present technology, therapy device controller 4240 is a dedicated motor control integrated circuit. For example, in one form a MC33035 brushless DC motor controller, manufactured by ONSEMI is used.

5.1.3.2.6 Protection Circuits

The one or more protection circuits 4250 in accordance with the present technology may comprise an electrical protection circuit, a temperature and/or pressure safety circuit.

5.1.3.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally, or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms described below.

5.1.3.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet, remote control, or other ancillary device.

5.1.3.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.1.3.2.9.1 Display Driver

A display driver 4292 receives as an input the characters, symbols, or images intended for display on the display 4294, and converts them to commands that cause the display 4294 to display those characters, symbols, or images.

5.1.3.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.1.3.3 RPT Device Algorithms

As mentioned above, in some forms of the present technology, the central controller 4230 may be configured to execute one or more algorithms expressed as computer programs stored in a non-transitory computer readable storage medium, such as memory 4260.

In other forms of the present technology, some portion or all of the algorithms may be implemented by a controller of an external device such as the local external device 4288 or the remote external device 4286. In such forms, data representing the input signals and/or intermediate algorithm outputs necessary for the portion of the algorithms to be executed at the external device may be communicated to the external device via the local external communication network 4284 or the remote external communication network 4282. In such forms, the portion of the algorithms to be executed at the external device may be expressed as computer programs stored in a non-transitory computer readable storage medium accessible to the controller of the external device. Such programs configure the controller of the external device to execute the portion of the algorithms to be executed at the external device.

Various algorithms helpful in implementing the disclosed therapy are described below.

5.1.4 Humidifier

Figure 5A:
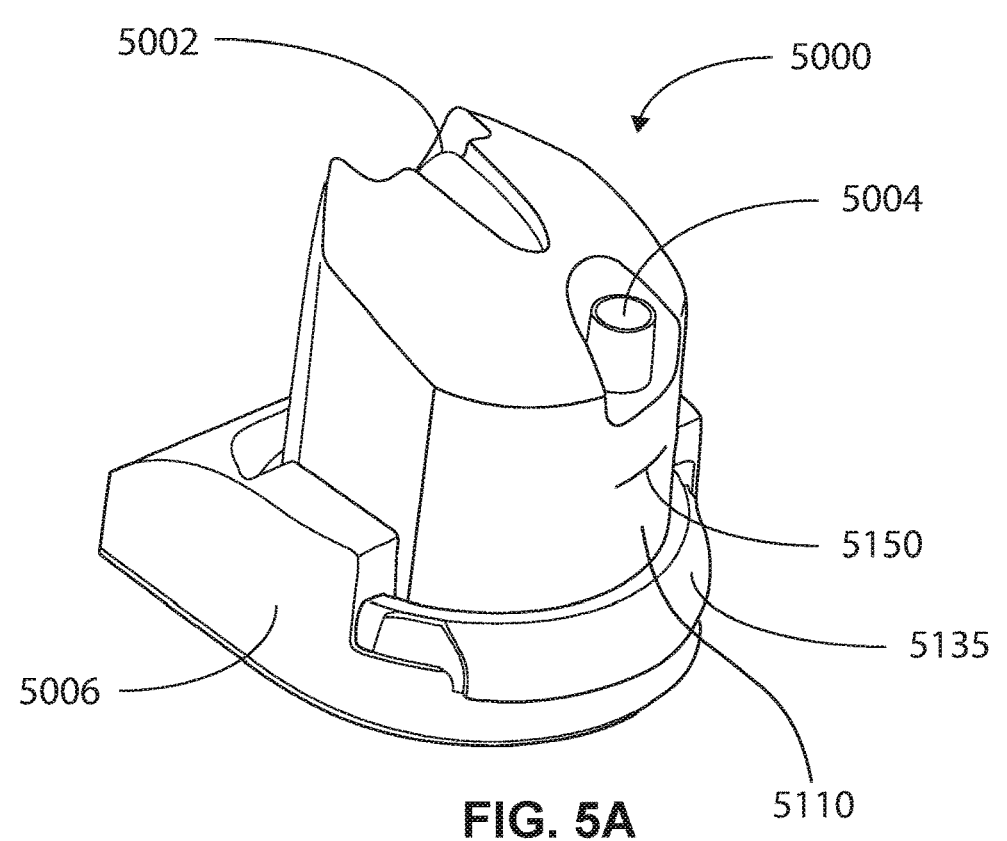
FIG. 5A shows an isometric view of a humidifier in accordance with one form of the present technology.

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

Figure 5B:
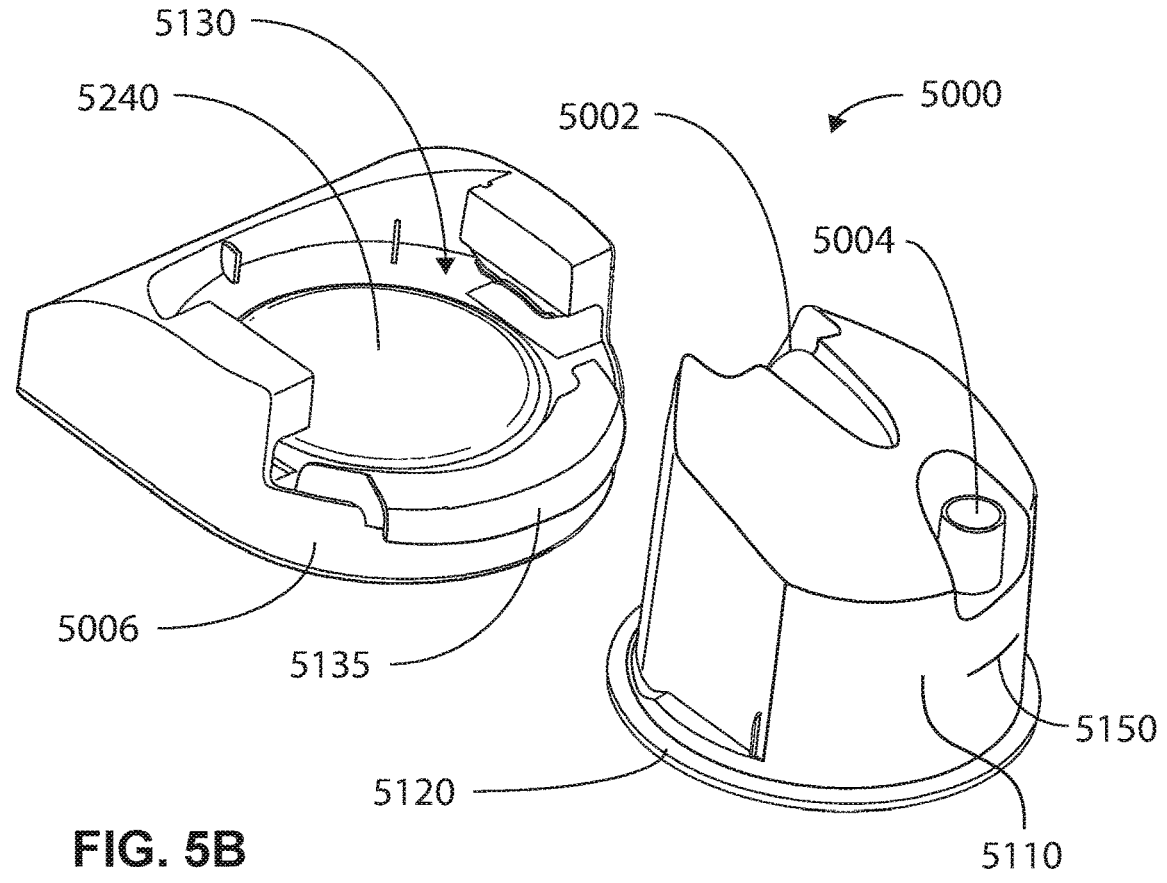
FIG. 5B shows an isometric view of a humidifier in accordance with one form of the present technology, showing a humidifier reservoir 5110 removed from the humidifier reservoir dock 5130.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240. Alternatively, a bubble humidifier 5000 may be employed.

5.1.5 Portable Oxygen Concentrator (POC)

Oxygen concentrators take advantage of pressure swing adsorption (PSA). Pressure swing adsorption may involve using a compressor to increase gas pressure inside a canister that contains particles of a gas separation adsorbent. As the pressure increases, certain molecules in the gas may become adsorbed onto the gas separation adsorbent. Removal of a portion of the gas in the canister under the pressurized conditions allows separation of the non-adsorbed molecules from the adsorbed molecules. The gas separation adsorbent may be regenerated by reducing the pressure, which reverses the adsorption of molecules from the adsorbent. Further details regarding oxygen concentrators may be found, for example, in U.S. Published Patent Application No. 2009/0065007, published Mar. 12, 2009, and entitled "Oxygen Concentrator Apparatus and Method", which is incorporated herein by reference.

Ambient air usually includes approximately 78% nitrogen and 21% oxygen with the balance comprised of argon, carbon dioxide, water vapour, and other trace gases. If a gas mixture such as air, for example, is passed under pressure through a vessel containing a gas separation adsorbent bed that attracts nitrogen more strongly than it does oxygen, part or all of the nitrogen will stay in the bed, and the gas coming out of the vessel will be enriched in oxygen. When the bed reaches the end of its capacity to adsorb nitrogen, it can be regenerated by reducing the pressure, thereby releasing the adsorbed nitrogen. It is then ready for another cycle of producing oxygen enriched air. By alternating canisters in a two-canister system, one canister can be collecting oxygen while the other canister is being purged (resulting in a continuous separation of the oxygen from the nitrogen). In this manner, oxygen can be accumulated out of the air for a variety of uses include providing supplementary oxygen to patients.

FIG. 7A contains a schematic diagram of a portable oxygen concentrator 100, according to one form of the present technology. Oxygen concentrator 100 may concentrate oxygen out of an air stream to provide oxygen enriched gas to a patient. As used herein, "oxygen enriched gas" is composed of at least about 50% oxygen, at least about 60% oxygen, at least about 70% oxygen, at least about 80% oxygen, at least about 90% oxygen, at least about 95% oxygen, at least about 98% oxygen, or at least about 99% oxygen.

Portable oxygen concentrator 100 may have a weight and size that allows the oxygen concentrator to be carried by hand and/or in a carrying case. As examples, oxygen concentrator 100 has a weight of less than about 20 lbs, less than about 15 lbs, less than about 10 lbs, or less than about 5 lbs. As examples, oxygen concentrator 100 has a volume of less than about 1000 cubic inches, less than about 750 cubic inches, less than about 500 cubic inches, less than about 250 cubic inches, or less than about 200 cubic inches.

Oxygen may be collected from ambient air by pressurising ambient air in canisters 302 and 304, which include a gas separation adsorbent. Gas separation adsorbents useful in an oxygen concentrator are capable of separating at least nitrogen from an air stream to produce oxygen enriched gas. Examples of gas separation adsorbents include molecular sieves that are capable of separation of nitrogen from an air stream. Examples of adsorbents that may be used in an oxygen concentrator include, but are not limited to, zeolites (natural) or synthetic crystalline aluminosilicates that separate nitrogen from oxygen in an air stream under elevated pressure. Examples of synthetic crystalline aluminosilicates that may be used include, but are not limited to: OXYSIV adsorbents available from UOP LLC, Des Plaines, IW; SYLOBEAD adsorbents available from W. R. Grace & Co, Columbia, MD; SILIPORITE adsorbents available from CECA S.A. of Paris, France; ZEOCHEM adsorbents available from Zeochem AG, Uetikon, Switzerland; and AgLi-LSX adsorbent available from Air Products and Chemicals, Inc., Allentown, PA.

As shown in FIG. 7A, air may enter the oxygen concentrator through air inlet 105. Air may be drawn into air inlet 105 by compression system 200. Compression system 200 may draw in air from the surroundings of the oxygen concentrator and compress the air, forcing the compressed air into one or both canisters 302 and 304. In one form, an inlet muffler 108 may be coupled to air inlet 105 to reduce sound produced by air being pulled into the oxygen concentrator by compression system 200. In one form, inlet muffler 108 may be a moisture and sound absorbing muffler. For example, a water absorbent material (such as a polymer water absorbent material or a zeolite material) may be used to both absorb water from the incoming air and to reduce the sound of the air passing into the air inlet 105.

Compression system 200 may include one or more compressors capable of compressing air. Pressurized air, produced by compression system 200, may be forced into one or both of the canisters 302 and 304. In some forms, the ambient air may be pressurized in the canisters to a pressure approximately in a range of 13-20 pounds per square inch (psi). Other pressures may also be used, depending on the type of gas separation adsorbent disposed in the canisters.

Coupled to each canister 302/304 are inlet valves 122/124 and outlet valves 132/134. As shown in FIG. 7A, inlet valve 122 is coupled to canister 302 and inlet valve 124 is coupled to canister 304. Outlet valve 132 is coupled to canister 302 and outlet valve 134 is coupled to canister 304. Inlet valves 122/124 are used to control the passage of air from compression system 200 to the respective canisters. Outlet valves 132/134 are used to release gas from the respective canisters during a venting process. In some forms, inlet valves 122/124 and outlet valves 132/134 may be silicon plunger solenoid valves. Other types of valves, however, may be used. Plunger valves offer advantages over other kinds of valves by being quiet and having low slippage.

In one form, pressurized air is sent into one of canisters 302 or 304 while the other canister is being vented. For example, during use, inlet valve 122 is opened while inlet valve 124 is closed. Pressurized air from compression system 200 is forced into canister 302, while being inhibited from entering canister 304 by inlet valve 124. A controller 400 is electrically coupled to valves 122, 124, 132, and 134. Controller 400 includes one or more processors 410 operable to execute program instructions stored in memory 420. The program instructions are adapted to configure the controller 400 to perform various predefined methods that are used to operate the oxygen concentrator 100. Memory 420 may include program instructions for operating inlet valves 122 and 124 out of phase with each other, i.e., when one of inlet valves 122 or 124 is opened, the other valve is closed. During pressurization of canister 302, outlet valve 132 is closed and outlet valve 134 is opened. Similar to the inlet valves, outlet valves 132 and 134 are operated out of phase with each other. In some forms, the voltages and the duration of the voltages used to open the input and output valves may be controlled by controller 400.

The controller 400 may include a transceiver 430 that may communicate with external devices to transmit data collected by the processor 410 or receive instructions from an external computing device for the processor 410.

Check valves 142 and 144 are coupled to canisters 302 and 304, respectively. Check valves 142 and 144 are one way valves that are passively operated by the pressure differentials that occur as the canisters are pressurized and vented. Check valves 142 and 144 are coupled to canisters to allow oxygen produced during pressurization of the canisters to flow out of the canister, and to inhibit back flow of oxygen or any other gases into the canisters. In this manner, check valves 142 and 144 act as one way valves allowing oxygen enriched gas to exit the respective canisters during pressurization.

The term "check valve", as used herein, refers to a valve that allows flow of a fluid (gas or liquid) in one direction and inhibits back flow of the fluid. Examples of check valves that are suitable for use include, but are not limited to: a ball check valve; a diaphragm check valve; a butterfly check valve; a swing check valve; a duckbill valve; and a lift check valve. Under pressure, nitrogen molecules in the pressurized ambient air are adsorbed by the gas separation adsorbent in the pressurized canister. As the pressure increases, more nitrogen is adsorbed until the gas in the canister is enriched in oxygen. The non-adsorbed gas molecules (mainly oxygen) flow out of the pressurized canister when the pressure reaches a point sufficient to overcome the resistance of the check valve coupled to the canister. In one form, the pressure drop of the check valve in the forward direction is less than 1 psi. The break pressure in the reverse direction is greater than 100 psi. It should be understood, however, that modification of one or more components would alter the operating parameters of these valves. If the forward flow pressure is increased, there is, generally, a reduction in oxygen enriched gas production. If the break pressure for reverse flow is reduced or set too low, there is, generally, a reduction in oxygen enriched gas pressure.

In one form, canister 302 is pressurized by compressed air produced in compression system 200 and passed into canister 302. During pressurization of canister 302 inlet valve 122 is open, outlet valve 132 is closed, inlet valve 124 is closed and outlet valve 134 is open. Outlet valve 134 is opened when outlet valve 132 is closed to allow substantially simultaneous venting of canister 304 while canister 302 is pressurized. Canister 302 is pressurized until the pressure in canister is sufficient to open check valve 142. Oxygen enriched gas produced in canister 302 exits through check valve and, in one form, is collected in accumulator 106.

After some time, the gas separation adsorbent will become saturated with nitrogen and will be unable to separate significant amounts of nitrogen from incoming air. This point is usually reached after a predetermined time of oxygen enriched gas production. In the form of the present technology described above, when the gas separation adsorbent in canister 302 reaches this saturation point, the inflow of compressed air is stopped and canister 302 is vented to remove nitrogen. During venting, inlet valve 122 is closed, and outlet valve 132 is opened. While canister 302 is being vented, canister 304 is pressurized to produce oxygen enriched gas in the same manner described above. Pressurization of canister 304 is achieved by closing outlet valve 134 and opening inlet valve 124. The oxygen enriched gas exits canister 304 through check valve 144.

During venting of canister 302, outlet valve 132 is opened allowing pressurized gas (mainly nitrogen) to exit the canister through concentrator outlet 130. In one form, the vented gases may be directed through muffler 133 to reduce the noise produced by releasing the pressurized gas from the canister. As gas is released from canister 302, the pressure in the canister drops, allowing the nitrogen to become desorbed from the gas separation adsorbent. The released nitrogen exits the canister through outlet 130, resetting the canister to a state that allows renewed separation of oxygen from an air stream. Muffler 133 may include open cell foam (or another material) to muffle the sound of the gas leaving the oxygen concentrator. In some forms, the combined muffling components/techniques for the input of air and the output of gas, may provide for oxygen concentrator operation at a sound level below 50 decibels.

During venting of the canisters, it is advantageous that at least a majority of the nitrogen is removed. In one form, at least about 50%, at least about 60%, at least about 70%, at least about 80%, at least about 90%, at least about 95%, at least about 98%, or substantially all of the nitrogen in a canister is removed before the canister is re-used to separate oxygen from air. In some forms, a canister may be further purged of nitrogen using an oxygen enriched stream that is introduced into the canister from the other canister.

In one form, a portion of the oxygen enriched gas may be transferred from canister 302 to canister 304 when canister 304 is being vented of nitrogen. Transfer of oxygen enriched gas from canister 302 to 304, during venting of canister 304, helps to further purge nitrogen (and other gases) from the canister. In one form, oxygen enriched gas may travel through flow restrictors 151, 153, and 155 between the two canisters. Flow restrictor 151 may be a trickle flow restrictor. Flow restrictor 151, for example, may be a 0.009 D flow restrictor (e.g., the flow restrictor has a radius 0.009" which is less than the diameter of the tube it is inside). Flow restrictors 153 and 155 may be 0.013 D flow restrictors. Other flow restrictor types and sizes are also contemplated and may be used depending on the specific configuration and tubing used to couple the canisters. In some forms, the flow restrictors may be press fit flow restrictors that restrict air flow by introducing a narrower diameter in their respective tube. In some forms, the press fit flow restrictors may be made of sapphire, metal or plastic (other materials are also contemplated).

Flow of oxygen enriched gas is also controlled by use of valve 152 and valve 154. Valves 152 and 154 may be opened for a short duration during the venting process (and may be closed otherwise) to prevent excessive oxygen loss out of the purging canister. Other durations are also contemplated. In one form, canister 302 is being vented and it is desirable to purge canister 302 by passing a portion of the oxygen enriched gas being produced in canister 304 into canister 302. A portion of oxygen enriched gas, upon pressurization of canister 304, will pass through flow restrictor 151 into canister 302 during venting of canister 302. Additional oxygen enriched air is passed into canister 302, from canister 304, through valve 154 and flow restrictor 155. Valve 152 may remain closed during the transfer process, or may be opened if additional oxygen enriched gas is needed. The selection of appropriate flow restrictors 151 and 155, coupled with controlled opening of valve 154 allows a controlled amount of oxygen enriched gas to be sent from canister 304 to 302. In one form, the controlled amount of oxygen enriched gas is an amount sufficient to purge canister 302 and minimize the loss of oxygen enriched gas through venting valve 132 of canister 302. While venting of canister 302 has been described, it should be understood that the same process can be used to vent canister 304 using flow restrictor 151, valve 152 and flow restrictor 153.

The pair of equalization/vent valves 152/154 work with flow restrictors 153 and 155 to optimize the air flow balance between the two canisters. This may allow for better flow control for venting the canisters with oxygen enriched gas from the other of the canisters. It may also provide better flow direction between the two canisters. It has been found that, while flow valves 152/154 may be operated as bi-directional valves, the flow rate through such valves varies depending on the direction of fluid flowing through the valve. For example, oxygen enriched gas flowing from canister 304 toward canister 302 has a flow rate faster through valve 152 than the flow rate of oxygen enriched gas flowing from canister 302 toward canister 304 through valve 152. If a single valve was to be used, eventually either too much or too little oxygen enriched gas would be sent between the canisters and the canisters would, over time, begin to produce different amounts of oxygen enriched gas. Use of opposing valves and flow restrictors on parallel air pathways may equalize the flow pattern of the oxygen between the two canisters. Equalising the flow may allow for a steady amount of oxygen available to the patient over multiple cycles and also may allow a predictable volume of oxygen to purge the other of the canisters. In some forms, the air pathway may not have restrictors but may instead have a valve with a built in resistance or the air pathway itself may have a narrow radius to provide resistance.

At times, oxygen concentrator may be shut down for a period of time. When an oxygen concentrator is shut down, the temperature inside the canisters may drop as a result of the loss of adiabatic heat from the compression system. As the temperature drops, the volume occupied by the gases inside the canisters will drop. Cooling of the canisters may lead to a negative pressure in the canisters. Valves (e.g., valves 122, 124, 132, and 134) leading to and from the canisters are dynamically sealed rather than hermetically sealed. Thus, outside air may enter the canisters after shutdown to accommodate the pressure differential. When outside air enters the canisters, moisture from the outside air may condense inside the canister as the air cools. Condensation of water inside the canisters may lead to gradual degradation of the gas separation adsorbents, steadily reducing ability of the gas separation adsorbents to produce oxygen enriched gas.

In one form, outside air may be inhibited from entering canisters after the oxygen concentrator is shut down by pressurising both canisters prior to shutdown. By storing the canisters under a positive pressure, the valves may be forced into a hermetically closed position by the internal pressure of the air in the canisters. In one form, the pressure in the canisters, at shutdown, should be at least greater than ambient pressure. As used herein the term "ambient pressure" refers to the pressure of the surroundings in which the oxygen concentrator is located (e.g. the pressure inside a room, outside, in a plane, etc.). In one form, the pressure in the canisters, at shutdown, is at least greater than standard atmospheric pressure (i.e., greater than 760 mmHg (Torr), 1 atm, 101,325 Pa). In one form, the pressure in the canisters, at shutdown, is at least about 1.1 times greater than ambient pressure; is at least about 1.5 times greater than ambient pressure; or is at least about 2 times greater than ambient pressure.

In one form, pressurization of the canisters may be achieved by directing pressurized air into each canister from the compression system and closing all valves to trap the pressurized air in the canisters. In one form, when a shutdown sequence is initiated, inlet valves 122 and 124 are opened and outlet valves 132 and 134 are closed. Because inlet valves 122 and 124 are joined together by a common conduit, both canisters 302 and 304 may become pressurized as air and or oxygen enriched gas from one canister may be transferred to the other canister. This situation may occur when the pathway between the compression system and the two inlet valves allows such transfer. Because the oxygen concentrator operates in an alternating pressurize/venting mode, at least one of the canisters should be in a pressurized state at any given time. In an alternative form, the pressure may be increased in each canister by operation of compression system 200. When inlet valves 122 and 124 are opened, pressure between canisters 302 and 304 will equalize, however, the equalized pressure in either canister may not be sufficient to inhibit air from entering the canisters during shutdown. In order to ensure that air is inhibited from entering the canisters, compression system 200 may be operated for a time sufficient to increase the pressure inside both canisters to a level at least greater than ambient pressure. Regardless of the method of pressurization of the canisters, once the canisters are pressurized, inlet valves 122 and 124 are closed, trapping the pressurized air inside the canisters, which inhibits air from entering the canisters during the shutdown period.

Referring to FIG. 7B, one form of an oxygen concentrator 100 is depicted. Oxygen concentrator 100 includes a compression system 200, a canister assembly 300 with air inlet 306, and a power supply 180 disposed within an outer housing 170. Outer housing 170 includes compression system inlets 105, cooling system passive inlet 101 at each end of outer housing 170, and outlet port 174. Inlets 101 are located in outer housing 170 to allow air from the environment to enter oxygen concentrator 100 to assist with cooling of the components in the compartment. Power supply 180 provides a source of power for the oxygen concentrator 100. Compression system 200 draws air in through the inlet 105 and muffler 108. Muffler 108 may reduce noise of air being drawn in by the compression system and also may include a desiccant material to remove water from the incoming air. Oxygen concentrator 100 may further include fan 172 used to vent air and other gases from the oxygen concentrator. Outlet port 174 is configured to attach to a conduit 192 (described below) to provide oxygen enriched gas produced by the oxygen concentrator 100 to a patient. Oxygen concentrator 100 may include a pressure sensor 176 coupled to controller 400 to determine an ambient pressure.

In one form, oxygen enriched gas produced in either of canisters 302 and 304 is collected in an oxygen accumulator 106 through check valves 142 and 144, respectively, as depicted schematically in FIG. 7A, before being provided to the patient.

5.1.5.1 Outlet System

FIG. 7C is a schematic diagram of an outlet system for an oxygen concentrator 100 according to one form of the present technology. A supply valve 160 may be situated within the gas flow path to control the release of the oxygen enriched gas from accumulator 106 to the patient. In one form, supply valve 160 is an electromagnetically actuated plunger valve. Supply valve 160 is actuated by controller 400 to control the delivery of oxygen enriched gas to a patient. Actuation of supply valve 160 is not timed or synchronized to the pressure swing adsorption process. Instead, actuation is, in POD therapy, synchronized to the patient's breathing, as described in more detail below.

Oxygen enriched gas in accumulator 106 passes through supply valve 160 into expansion chamber 162 as depicted in FIG. 7C. Oxygen enriched gas in expansion chamber 162 builds briefly, through release of gas from accumulator 106 by supply valve 160, and then is bled through a small orifice flow restrictor 175 to a flow rate sensor 185 and then to particulate filter 187. Flow restrictor 175 may be a 0.025 D flow restrictor. Other flow restrictor types and sizes may be used. In some forms, the diameter of the flow restrictor 175 may be variable by the controller 400 to allow the controller 400 to control the flow rate of delivered oxygen enriched gas. Flow rate sensor 185 may be any sensor capable of estimating the flow rate of oxygen enriched gas flowing through the conduit. Particulate filter 187 may be used to filter bacteria, dust, granule particles, etc., prior to delivery of the oxygen enriched gas to the patient. The oxygen enriched gas passes through filter 187 to connector 190 which sends the oxygen enriched gas to the patient via outlet port 174 and to pressure sensor 194.

Expansion chamber 162 may include one or more oxygen sensors 165 capable of being used to determine an oxygen concentration of gas passing through the chamber. An oxygen sensor is a device capable of detecting oxygen in a gas. Examples of oxygen sensors include, but are not limited to, ultrasonic oxygen sensors, electrical oxygen sensors, and optical oxygen sensors. In one form, oxygen sensor 165 is an ultrasonic oxygen sensor that includes an ultrasonic emitter 166 and an ultrasonic receiver 168. In some forms, ultrasonic emitter 166 may include multiple ultrasonic emitters and ultrasonic receiver 168 may include multiple ultrasonic receivers. In forms having multiple emitters/receivers, the multiple ultrasonic emitters and multiple ultrasonic receivers may be axially aligned (e.g., transverse to the gas mixture flow path, which may be perpendicular to the axial alignment).

Flow rate sensor 185 may be used to determine the flow rate of oxygen enriched gas flowing through the outlet system. Flow rate sensors that may be used include, but are not limited to: diaphragm/bellows flow meters; rotary flow meters (e.g. Hall effect flow meters); turbine flow meters; orifice flow meters; and ultrasonic flow meters. Flow rate sensor 185 may be coupled to controller 400.

In some forms, oxygen sensor 165 and flow rate sensor 185 may provide a measurement of an actual amount of oxygen being provided. For example, flow rate sensor 185 may measure a volume of gas (based on flow rate) provided and ultrasonic sensor system 165 may measure the concentration of oxygen of the oxygen enriched gas provided. These two measurements together may be used by controller 400 to determine an approximation of the actual amount of oxygen provided to the patient.

Oxygen enriched gas passes through flow rate sensor 185 to filter 187. The filtered oxygen enriched gas passes through filter 187 to connector 190. Connector 190 may be a "Y" connector coupling the outlet of filter 187 to pressure sensor 194 and outlet port 174. Pressure sensor 194, which is coupled to controller 400, may be used to monitor the pressure of the oxygen enriched gas passing through outlet port 174 to the patient.

Oxygen enriched gas may be provided to a patient through an outlet conduit 192 connected to outlet port 174. In one form, conduit 192 may be a silicone tube. Conduit 192 may be coupled to a patient using a patient interface 196, as depicted in FIG. 7D. Patient interface 196 is positioned proximate to a patient's airway (e.g., proximate to the patient's mouth and/or nose) to allow delivery of the oxygen enriched gas to the patient while allowing the patient to breathe air from the surroundings. Patient interface 196 may be any device capable of providing the oxygen enriched gas to nasal cavities or oral cavities. Examples of patient interfaces include, but are not limited to: nasal masks, nasal pillows, nasal prongs, nasal cannulas, and mouthpieces. Patient interface 196 is depicted as a nasal cannula in FIG. 7D. One example of such a nasal cannula being worn by a patient 1000 is illustrated as 3800 in FIG. 3.

5.1.5.2 Triggering Bolus Delivery

As mentioned above, in POD mode, oxygen enriched gas is provided to the patient in synchrony with the breathing cycle. In order to minimize the amount of oxygen enriched gas that is needed to be produced, or conversely to minimise the wastage of oxygen enriched gas delivered during exhalation, controller 400 may be configured to synchronise delivery of the oxygen enriched gas with the patient's inhalations. Reducing the amount of oxygen delivered may reduce the amount of air compression needed for oxygen concentrator 100 (and consequently may reduce the power demand from the compressors).

In POD mode, oxygen enriched gas produced by oxygen concentrator 100 is stored in an oxygen accumulator 106 and released by supply valve 160 to the patient as a pulse or "bolus" as the patient inhales. In some implementations, the bolus comprises a rectangular pulse whose flow rate of oxygen is constant throughout its duration.

Additional methods of determining the timing of the opening of the supply valve 160 by the controller 400 so as to deliver oxygen in POD mode are described below.

5.2 Anti-Infection Therapy

In one form of the present technology, the central controller 4230 controls the pressure generator 4140 to deliver a flow of air through the air circuit 4170 such that the device flow rate Qd is equal to a target flow rate Qt(t) which varies periodically with time t in synchrony with the breathing cycle. The target flow rate Qt(t) is chosen so as to lessen the risk of infection from inhalation of ambient pathogens. In some forms, the target flow rate Qt(t) follows a profile that just exceeds the patient's instantaneous respiratory flow rate Qr(t) throughout the inspiratory portion of the breathing cycle, and has a constant value (e.g. zero) throughout the expiratory portion. Such a target flow rate profile Qt(t) prevents entrainment of ambient air by the patient during inspiration. As a result, the risk of infection from nasal inhalation of ambient pathogens is greatly diminished.

Setting a target flow rate profile Qt(t) that just exceeds the patient's instantaneous respiratory flow rate during inspiration corresponds with ensuring that the patient's nasal pressure Pn is always positive with respect to ambient, since if the nasal pressure is negative during inspiration, there will be entrainment of air from ambient to meet demand.

In addition, with a reduced flow rate, such as zero, during the expiratory portion, power consumption of the RPT device 4000 is reduced compared to conventional high flow therapy, as is any drying effect from the air flow.

To implement this anti-infection therapy, the central controller 4230 of the RPT device 4000 may be configured to execute one or more algorithms expressed as computer programs, or modules thereof, stored in a non-transitory computer readable storage medium, such as memory 4260, as described above. In general, each algorithm or module receives as an input a signal from a transducer 4270 of the RPT device 4000, for example a flow rate sensor 4274 or a pressure sensor 4272, and performs one or more process steps to calculate one or more output values. The output values may be used as inputs to another algorithm or module.

FIG. 8 is a flow chart illustrating a method 8000 for implementing the disclosed anti-infection therapy according to one form of the present technology. The steps of the method 8000 may represent algorithms or modules executed by the central controller 4230 as described above.

The method 8000 starts at step 8010, which estimates a peak inspiratory flow rate $Q_{peak}$ for the patient 1000. Step 8010 will be described in further detail below with reference to FIG. 9.

Step 8020 follows, at which the central controller computes an initial target flow rate profile Qt(t) from the peak inspiratory flow rate $Q_{peak}$ estimated at step 8010. The initial target flow rate profile Qt(t) is computed to slightly exceed the patient's minimum inspiratory flow rate profile $Q_{in(min)}$(t) during inspiration by a predetermined or a computed margin function of the patient's breathing.

The shape of the minimum inspiratory flow rate profile $Q_{in(min)}$(t) of a spontaneously breathing patient can be approximated by a template function q(t) that rises from 0 to 1 and returns to 0 over the interval [0, 1]. Step 8020 fits such a template function q(t) to the patient's peak inspiratory flow rate $Q_{peak}$ and inspiratory time $T_I$ to generate a minimum inspiratory flow rate profile $Q_{in(min)}$(t) for the patient.

In one implementation of step 8020, the template function q(t) is a sinusoidal half-wave (q(t)=sin(πt)), so the minimum inspiratory flow rate profile $Q_{in(min)}$(t) takes the form of a sinusoidal half-wave of peak value $Q_{peak}$ and duration equal to the inspiratory time $T_I$:

$$Q_{in(min)}(t) = Q_{peak} \sin\left(\frac{\pi t}{T_I}\right), 0 \leq t \leq T_I \qquad (1)$$

The inspiratory time $T_I$ may be set to a typical value such as 1.6 seconds (see FIG. 6). Alternatively, an estimate $\tilde{T}_I$ of the patient's actual inspiratory time, obtained from step 8025 (described below), may be used as the inspiratory time $T_I$. In one implementation, Step 8020 sets the initial target flow rate profile Qt(t) to:

the minimum inspiratory flow rate profile $Q_{in(min)}$(t) of the patient plus a margin function ΔQ, during inspiration; zero, during expiration.

The margin function ΔQ is chosen to compensate for likely error in using the minimum inspiratory flow rate profile $Q_{in(min)}$(t) to approximate the patient's actual inspiratory flow rate profile and thereby achieve the marginal increase over the patient's actual inspiratory flow rate profile. In one implementation, the margin function ΔQ is a predetermined amount, for example 1 litre per minute. In another implementation, the margin function is a percentage (e.g., a predetermined percentage) of the patient's peak inspiratory flow rate. Such a percentage may be in a range of 10% to 30%, of the peak inspiratory flow rate $Q_{peak}$, e.g. 20% of $Q_{peak}$.

In another implementation, the margin function ΔQ may be set to the minimum inspiratory flow rate profile $Q_{in(min)}$(t) of the patient multiplied by a factor that is slightly or marginally greater than zero, for example 0.1 or another factor in a range, for example, of 0.1 to 0.3. In this implementation the margin function rises and then falls over the inspiratory portion, peaking at the instant of peak inspiratory flow rate.

At step 8030, the central controller 4230 commences therapy, which comprises controlling setting the device flow rate Qd to match the target flow rate profile Qt(t) in synchrony with the breathing cycle of the patient. Conventional closed-loop control strategies such as PI control, using the signal from the flow rate sensor 4274 as the feedback variable, may be employed to implement step 8030.

At step 8040, the central controller 4230 enters a loop (e.g., a repeated process or processes) which repeatedly adjusts the target flow rate profile Qt(t) according to the patient's actual breathing patterns. The loop comprising steps 8040, 8050, and 8060 is optional and need not be executed if the initial target flow rate profile Qt(t) is used, or otherwise deemed satisfactory, for the entire therapy session. The adjustment associated with the loop is based on estimating the nasal pressure Pn during therapy, and adjusting the target flow rate profile Qt(t) in response to the estimated nasal pressure Pn.

Steps 8030 and 8060, and optionally steps 8010 and 8020, may use input from step 8025, which is a parallel step that estimates the timing of the patient's breathing using one or more signals from respective transducers 4270 of the RPT device 4000, independently of the rest of the method 8000. Step 8025 may be carried out before therapy begins, and/or during therapy, either once or repeatedly, by observing the patient's breathing using any one or more of the transducers 4270. Step 8025 provides step 8030 with the starting instant of each inspiration (trigger point) and the starting instant of each expiration (cycle point), to enable synchrony. Step 8025 also provides step 8060 with estimates $\tilde{T}_I$ of the patient's inspiratory time. Step 8025 may also provide step 8010 with an estimate $\tilde{R}_b$ of the patient's breathing rate and an estimate $\tilde{T}_I$ of the patient's inspiratory time. Step 8025 may also provide step 8020 with the estimate $\tilde{T}_I$ of the patient's inspiratory time. Step 8025 will be described in more detail below in relation to FIG. 10.

Step 8040 estimates the patient's nasal pressure Pn over the inspiratory portion. Step 8040 may optionally use the signals from the flow rate sensor 4274 and/or the pressure sensor 4272, representing the device flow rate Qd and the device pressure Pd respectively. In one implementation, the nasal pressure Pn may be estimated by subtracting a pressure drop ΔP along the air circuit 4170 to the ends of the prongs of the patient interface 3800 from the device pressure Pd. The pressure drop ΔP varies with the device flow rate Qd according to a characteristic function of the air circuit/patient interface combination. The characteristic may be obtained from a calibration procedure during which the device pressure Pd is recorded in a table for a range of device flow rate values Qd. This calibration procedure may be carried out before the patient interface 3800 is donned by the patient 1000, so that the pressure at the ends of the prongs of the patient interface 3800 may be taken as ambient pressure, and the pressure drop ΔP for each device flow rate value Qd is therefore equal to the device pressure Pd.

Alternatively, if the type of patient interface 3800 is known or may be identified by other means, the characteristic may be obtainable from a pre-determined look-up table of characteristic function parameters.

Step 8050 then adjusts the peak inspiratory flow rate Qpeak of the patient based on the nasal pressure Pn estimated at step 8040. In general, step 8050 increases the peak inspiratory flow rate Qpeak if a value $\tilde{P}_n$ representative of the nasal pressure Pn over the inspiratory portion is below a target value Pnt, and decreases the peak inspiratory flow rate Qpeak if the representative value $\tilde{P}_n$ is above the target value Pnt. In some forms, the representative value $\tilde{P}_n$ may be a minimum value of the nasal pressure Pn over the inspiratory portion, or (in other forms) some combination (e.g. an average) of minimum values over plural consecutive inspiratory portions may be used. In one implementation, a target value Pnt of zero is used, which will reduce the entrained room air being inhaled by the patient to the extent that the representative value $\tilde{P}_n$ is negative.

The adjustment to the peak inspiratory flow rate Qpeak may be computed by conventional control methods, e.g. PI control, in which a decrement ΔQpeak to the peak inspiratory flow rate Qpeak is proportional to the difference between the representative value $\tilde{P}_n$ and the target value Pnt.

Step 8060 then computes a new target flow rate profile Qt(t) based on the adjusted peak inspiratory flow rate Qpeak. Step 8060 is the same as step 8020, except that step 8060 may use a current estimate $\hat{T}_I$ of the patient's inspiratory time from step 8025 rather than a typical value. Finally, the method 8000 returns to step 8030 to continue therapy with the adjusted target flow rate profile Qt(t).

FIG. 9 is a flow chart illustrating a method 9000 of estimating the patient's peak inspiratory flow rate Qpeak, which may be applied by the controller 4230 to implement step 8010 of the method 8000.

The method 9000 starts at step 9010, which estimates the patient's anatomic deadspace. Anatomic dead space is approximately correlated to a person's height, and effectively imposes a per-breath augmentation of tidal volume. Step 9010 may therefore estimate the patient's anatomic deadspace $VD_{an}$ based on their height. The patient's height (H) may be manually entered to the RPT device 4000 via its input device 4220 and stored in the memory 4260 for access by the controller 4230 for generating the estimate. In one implementation, step 9010 may use the function:

$$VD_{an} = 7.585 \times 10^{-4} \times H(\text{cm})^{2.363} \qquad (2)$$

Step 9020 then estimates the patient's minimum sustainable alveolar ventilation. Mammals possess a minimum resting energy expenditure, also called basal metabolic rate, and in the case of human beings this quantity can be loosely estimated from a person's height (or length for infants). The associated metabolism produces a minimum volume of $CO_2$, i.e. demands a minimum alveolar ventilation. Step 9020 may therefore use the patient's height to estimate the patient's minimum alveolar minute ventilation. In one implementation, the patient's resting energy expenditure (REE) is estimated from their height, and the REE is used to estimate the patient's minimum alveolar minute ventilation, $\dot{V}_{ALV(min)}$.

In one implementation, the patient's REE may be estimated from the patient's height in centimetres as a piecewise linear interpolation between, for example four, breakpoints: H=40, 90, 140, and 190 cm. The corresponding REE values (in Megajoules per day) at each height breakpoint may be as follows:

$$REE(40 \text{ cm}) = 0.11$$

$$REE(90 \text{ cm}) = 3.14$$

$$REE(140 \text{ cm}) = 4.82$$

$$REE(190 \text{ cm}) = 7.35 \qquad (3)$$

In other implementations, alternative estimates for REE may be made based on other patient parameters such as age, weight, and gender and other number of breakpoints.

In one implementation, step 9020 then estimates the patient's minimum alveolar minute ventilation, $\dot{V}_{ALV(min)}$, in litres per minute, from the patient's resting energy expenditure (REE) as follows:

$$\dot{V}_{ALV(min)} = REE \times ActivityFactor \times \left( \frac{P_{amb} - 47 \text{ mmHg}}{PACO_2} \right) \qquad (4)$$

where $PACO_2$ is the arterial pressure of $CO_2$ in the bloodstream (typically 40 mmHg, but can range as high as 60 mmHg for hypercapnic patients), Pamb is the ambient pressure (typically 760 mmHg at sea level) and ActivityFactor is a factor that is unity for resting, but can increase up to 2 for high activity levels. Setting ActivityFactor to unity gives an acceptable minimum alveolar minute ventilation, $\dot{V}_{ALV(min)}$.

Step 9030 estimates the patient's average minimum tidal volume $V_{T(min)}$ from the patient's minimum alveolar minute ventilation, $\dot{V}_{ALV(min)}$ from step 9020, a breathing rate Rb, and the anatomic deadspace $VD_{an}$ from step 9010 as follows:

$$V_{T(min)} = VD_{an} + \frac{\dot{V}_{ALV(min)}}{Rb} \qquad (5)$$

The breathing rate Rb may be set to a typical maximum resting value such as 15 BPM (see FIG. 6). Finally, step 9040 estimates the patient's peak inspiratory flow rate $Q_{peak}$ from the minimum tidal volume $V_{T(min)}$ and an inspiratory time $T_I$ using the following definition of tidal volume as the volume of inspired flow over the inspiratory time $T_I$:

$$V_{T(min)} = \int_0^{T_I} Q_{peak} q\left( \frac{t}{T_i} \right) dt \qquad (6)$$

where q(t) is the inspiratory template function mentioned above. In implementations in which the template function q(t) is the sinusoidal half-wave mentioned above, step 9040 may calculate the patient's peak inspiratory flow rate $Q_{peak}$ via the following formula obtained from equation (6):

$$Q_{peak} = \frac{\pi}{2} \frac{V_{T(min)}}{T_I} \qquad (7)$$

The inspiratory time $T_I$ may be set to a typical value such as 1.6 seconds (see FIG. 6).

In other implementations, other template functions q(t) may be used, e.g. a raised cosine (squared sine), parabola, root sine, or sine to the power of 0.7. In such implementations there will be a different relationship between the peak inspiratory flow rate $Q_{peak}$ and the minimum tidal volume $V_{T(min)}$ than that expressed in equation (7). The relationship is derivable from equation (6) using the chosen template function q(t).

In other implementations of step 8010, actual estimates $\hat{R}_b$ and $\hat{T}_I$ of the patient's breathing rate and inspiratory time, obtained from step 8025, may be used in steps 9030 and 9040 respectively.

FIG. 10 is a flow chart illustrating a method 10000 of estimating the patient's breath timing, which may be applied by the controller 4230 to implement step 8025 of the method 8000.

The method 10010 starts at step 10010, which may optionally use the signals from the flow rate sensor 4274 and/or the pressure sensor 4272, representing the device flow rate Qd and the device pressure Pd respectively. It may be shown that either or both of these sensed parameters are indicative of the breathing cycle of the patient. Step 10010 computes the overall (circuit plus patient) conductance by dividing the device flow rate Qd by the device pressure Pd, or the overall impedance by dividing the device pressure Pd by the device flow rate Qd. Given the changing nature of the signals that are applied to the computation of conductance and/or impedance, the determined conductance and imped-ance, as time varying signals, each have an alternating component AC (e.g., concerning frequency). In this regard, it may be shown that the AC component of both the overall conductance and the overall impedance varies in synchrony with the respiratory flow rate Qr. The AC component of the overall conductance increases as the patient's respiratory flow rate Qr increases in a positive sense during inspiration, while the AC component of the overall impedance decreases. Likewise, the AC component of the overall conductance decreases as the patient's respiratory flow rate Qr increases in a negative sense during expiration, while the AC component of the overall impedance increases. Using the conductance or the impedance has the advantage over using just the device pressure Pd or just the device flow rate Qd of relative immunity to the applied therapy pressure or flow rate.

Step 10020 therefore extracts the AC component of the overall impedance or the overall conductance. This compo-nent is referred to as the dynamic conductance or the dynamic impedance. In one implementation, step 10020 high-pass filters the overall conductance or impedance using a cutoff frequency that is well below the typical human breathing rate, e.g. in the range of 0.01 Hz to 0.1 Hz, to generate the dynamic signals. Step 10030 then extracts the trigger and cycle points of the patient's breathing from the dynamic conductance signal or dynamic impedance signal. In one implementation, step 10030 extracts the zero-cross-ing points of the dynamic conductance or impedance signals to determine the trigger points (starts of inspiration) and cycle points (starts of expiration). The trigger points are the positive-going zero-crossing points of the dynamic conduc-tance and the negative-going zero-crossing points of the dynamic impedance, and vice versa for the cycle points.

Step 10030 then estimates the total time Ttot by deter-mining the duration of one or more intervals between consecutive trigger points, or consecutive cycle points. In one implementation of step 10030, the estimated total time Ttot may be calculated as the moving average of the durations of several successive such intervals. The estimated breathing rate $\tilde{R}_b$ is then the reciprocal of the total time estimate Ttot, expressed in BPM. Step 10030 may also estimate the inspiratory time $T_I$ from the duration of one or more inspiratory portions, between consecutive trigger point/cycle point pairs. In one implementation of step 10030, the estimated inspiratory time $\tilde{T}_I$ is the moving average of the duration of several successive such inspira-tory portions.

5.2.1 Supplementary Oxygen

As mentioned above, in some implementations of the disclosed anti-infection therapy, supplementary oxygen 4180 may be delivered to one or more points in the pneu-matic path, such as that of the RPT device 4000. The supplementary oxygen may be delivered from a POC 100, or from an oxygen cylinder coupled to a device known as a conserver, which uses a valve to regulate the flow rate and timing of the oxygen released from the cylinder. As men-tioned above, to minimise wastage the oxygen may be delivered in POD mode, i.e. as a series of boluses in synchrony with the patient's inspiration. In one implemen-tation, the controller 400 of a POC 100, or the equivalent device in a conserver, may be configured to communicate with the central controller 4230 of the RPT device to synchronise of delivery of the bolus in relation to the anti-infection therapy provided by the RPT device according to any of the example control methodologies as previously described. For example, through step 8025, the controller 4230 may provide the starting instant of each inspiration (trigger points) to the flow rate control step 8030. In one implementation, the central controller 4230 may also pro-vide the trigger points to the controller 400 of the POC 100, which opens the supply valve 160 to release a bolus of oxygen based on each trigger point. Depending on where the oxygen is to be delivered, the controller 400 may open the supply valve at the trigger point, or somewhat before it to compensate for the propagation delay of the oxygen bolus down the air circuit, so that the bolus arrives at the patient's airway at the optimum time to minimise waste. Further details as to how to optimise the timing of delivery of POD mode supplementary oxygen in a respiratory therapy air circuit may be found in the co-pending Australian provi-sional application no. 2018903114 titled "Methods and apparatus for treating respiratory disorders".

5.3 Glossary

For the purposes of the present technology disclosure, in certain forms of the present technology, one or more of the following definitions may apply. In other forms of the present technology, alternative definitions may apply.

5.3.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the therapy system or patient, and (ii) immediately surrounding the therapy system or patient.

For example, ambient pressure may be the pressure immediately surrounding or external to the body.

Continuous Positive Airway Pressure (CPAP) therapy: Respiratory pressure therapy in which the treatment pressure is approximately constant through a breathing cycle of a patient. In some forms, the pressure at the entrance to the airways will be slightly higher during exhalation, and slightly lower during inhalation. In some forms, the pressure will vary between different breathing cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air being delivered by the RPT device, while the target flow rate, which represents a target value to be achieved by the device flow rate Qd at the current instant of time, is given the symbol Qt. Vent flow rate, Qv, is the flow rate of air passing through a vent. Respiratory flow rate, Qr, is the flow rate of air that is received into the patient's respiratory system.

Humidifier: A humidifying apparatus constructed and arranged, or configured with a physical structure to be capable of providing a therapeutically beneficial amount of water ($H_2O$) vapour to a flow of air to ameliorate a medical respiratory condition of a patient.

Patient: A person, whether or not they are suffering from a respiratory condition.

Pressure: Force per unit area. Pressure may be expressed in a range of units, including $cmH_2O$, g-f/cm$^2$ and hectopascal. 1 $cmH_2O$ is equal to 1 g-f/cm$^2$ and is approximately 0.98 hectopascal. In this specification, unless otherwise stated, pressure is given relative to ambient pressure in units of $cmH_2O$, so ambient pressure is zero, above-ambient pressure is positive, and below-ambient pressure is negative.

The pressure in the pneumatic path proximal to an outlet of the pneumatic block (the device pressure) is given the symbol Pd. The pressure in the patient interface (the interface pressure) is given the symbol Pm. The pressure within the nose (the nasal pressure) is given the symbol Pn.

Respiratory Pressure Therapy: The application of a supply of air to an entrance to the airways at a treatment pressure that is typically positive with respect to atmosphere.

Ventilator: A mechanical device that provides pressure support to a patient to perform some or all of the work of breathing.

5.3.2 Breathing Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate (Rb): The rate of spontaneous respiration of a patient, usually measured in breaths per minute.

Duty cycle: The ratio of inspiratory time $T_I$ to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory or expiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

Inspiratory time ($T_I$): The duration of the inspiratory portion of the respiratory flow rate waveform.

Expiratory Time (Te): The duration of the expiratory portion of the respiratory flow rate waveform.

Total Time (Ttot): The total duration between the start of one inspiratory portion of a respiratory flow rate waveform and the start of the following inspiratory portion of the respiratory flow rate waveform (the reciprocal of breathing rate Rb).

Typical recent ventilation: The value of ventilation around which recent values of ventilation over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation: A measure of a rate of gas respiration. Measures of ventilation may include one or both of inspiratory and expiratory flow volumes, per unit time. When expressed as a volume per minute, this quantity is often referred to as "minute ventilation". Minute ventilation is sometimes given simply as a volume, understood to be the volume per minute. Alveolar ventilation is a measure of the rate of gas exchange by the patient's respiratory system, which is less than the rate of gas being respiration.

5.3.3 Ventilation

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired interface pressure which the ventilator will attempt to achieve at a given time.

Inspiratory positive airway pressure (IPAP): Maximum desired interface pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP–EPAP). In some contexts, pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous Timed (S T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator, or other device such as an RPT device, delivers a breath of air to a spontaneously breathing patient, it is said to be triggered to do so. Triggering usually takes place at or near the initiation of the respiratory portion of the breathing cycle by the patient's efforts.

5.4 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.5 REFERENCE SIGNS LIST

| | |
|---|---|
| portable oxygen concentrator | 100 |
| cooling system passive inlet | 101 |
| compression system inlets | 105 |
| inlet muffler | 108 |
| accumulator | 106 |
| inlet valves | 122 |
| inlet valves | 124 |
| outlet | 130 |
| outlet valves | 132 |
| muffler | 133 |
| outlet valves | 134 |
| check valves | 142 |
| check valves | 144 |
| flow restrictor | 151 |
| valves | 152 |
| flow restrictors | 153 |
| valves | 154 |
| flow restrictor | 155 |
| supply valve | 160 |
| expansion chamber | 162 |
| oxygen sensor | 165 |
| ultrasonic emitter | 166 |
| ultrasonic receiver | 168 |
| outer housing | 170 |
| fan | 172 |
| outlet port | 174 |
| flow restrictor | 175 |
| pressure sensor | 176 |
| power supply | 180 |
| flow rate sensor | 185 |
| filter | 187 |
| connector | 190 |
| conduit | 192 |
| pressure sensor | 194 |
| patient interface | 196 |
| compression system | 200 |
| canister assembly | 300 |
| canister | 302 |
| canister | 304 |
| air inlet | 306 |
| controller | 400 |
| processors | 410 |
| memory | 420 |
| patient | 1000 |
| patient interface | 3000 |
| nasal cannula-type unsealed patient interface | 3800 |
| nasal prongs | 3810a |
| nasal prongs | 3810b |
| air supply lumens | 3820a |
| air supply lumens | 3820b |
| RPT device | 4000 |
| external housing | 4010 |
| upper portion | 4012 |
| portion | 4014 |
| panel | 4015 |
| chassis | 4016 |
| handle | 4018 |
| pneumatic block | 4020 |
| air filters | 4110 |
| inlet air filter | 4112 |
| outlet air filter | 4114 |
| mufflers | 4120 |
| inlet muffler | 4122 |
| outlet muffler | 4124 |
| pressure generator | 4140 |
| blower | 4142 |
| motor | 4144 |

-continued 5.5 REFERENCE SIGNS LIST

| | |
|---|---|
| anti - spill back valve | 4160 |
| air circuit | 4170 |
| supplementary oxygen | 4180 |
| electrical components | 4200 |
| Printed Circuit Board Assembly | 4202 |
| power supply | 4210 |
| input device | 4220 |
| central controller | 4230 |
| clock | 4232 |
| therapy device controller | 4240 |
| protection circuits | 4250 |
| memory | 4260 |
| respective transducers | 4270 |
| pressure sensors | 4272 |
| flow rate sensor | 4274 |
| motor speed transducer | 4276 |
| data communication interface | 4280 |
| remote external communication network | 4282 |
| local external communication network | 4284 |
| remote external device | 4286 |
| local external device | 4288 |
| output device | 4290 |
| display driver | 4292 |
| display | 4294 |
| therapy control module | 4330 |
| humidifier | 5000 |
| humidifier inlet | 5002 |
| humidifier outlet | 5004 |
| humidifier base | 5006 |
| humidifier reservoir | 5110 |
| humidifier reservoir dock | 5130 |
| heating element | 5240 |
| method | 8000 |
| step | 8010 |
| step | 8020 |
| step | 8025 |
| step | 8030 |
| step | 8040 |
| step | 8050 |
| step | 8060 |
| method | 9000 |
| step | 9010 |
| step | 9020 |
| step | 9030 |
| step | 9040 |
| method | 10000 |
| step | 10010 |
| step | 10020 |
| step | 10030 |
| step | 10040 |

The invention claimed is:

1. A method of a controller controlling setting of a respiratory flow therapy device for an anti-infection therapy, the method comprising:

computing, by the controller of the respiratory flow therapy device, a target flow rate profile for a patient using a margin function of the patient's breathing, wherein computing the target flow rate profile during inspiration comprises adding the margin function to a minimum inspiratory flow rate profile of the patient's inspiration such that the target flow rate profile exceeds, according to the margin function, the minimum inspiratory flow rate profile, wherein the computing fits a template function, the template function having a shape, to a peak inspiratory flow rate of the patient and an inspiratory time to generate the minimum inspiratory flow rate profile; and controlling setting of the respiratory flow therapy device to generate a flow of air with the respiratory flow therapy device according to the target flow rate profile, wherein the generation is in synchrony with a sensed parameter that is indicative of a breathing cycle of the patient.

2. The method of claim 1 wherein the margin function is configured such that the target flow rate profile marginally exceeds the minimum inspiratory flow rate profile of the patient.

3. The method of claim 1, wherein the computing comprises:

computing the minimum inspiratory flow rate profile of the patient.

4. The method of claim 1, wherein the margin function is a function of the peak inspiratory flow rate.

5. The method of claim 4, further comprising estimating the peak inspiratory flow rate.

6. The method of claim 4, wherein the function of the peak inspiratory flow rate comprises a percentage.

7. The method of claim 6, wherein the percentage is in a range of 10 to 30 percent.

8. The method of claim 1, wherein the margin function comprises a multiple of the minimum inspiratory flow rate profile.

9. The method of claim 8, wherein the multiple is in a range of 0.1 to 0.3.

10. The method of claim 3, wherein computing the minimum inspiratory flow rate profile comprises:

estimating the peak inspiratory flow rate of the patient based on the patient's height, and computing the minimum inspiratory flow rate profile from the peak inspiratory flow rate.

11. The method of claim 10, wherein estimating the peak inspiratory flow rate comprises computing an estimate of anatomic deadspace, computing an estimate of minimum ventilation, and computing an estimate of minimum tidal volume.

12. The method of claim 1, wherein computing the target flow rate profile during expiration comprises setting the target flow rate profile to zero.

13. The method of claim 1, further comprising:

computing a new target flow rate profile for the patient, and controlling setting of the respiratory flow therapy device to further generate a flow of air with the respiratory flow therapy device according to the new target flow rate profile, wherein the further generation is in synchrony with a sensed parameter that is indicative of a subsequent breathing cycle of the patient.

14. The method of claim 13, wherein computing the new target flow rate profile comprises:

estimating at least one value of nasal pressure of the patient over an inspiratory portion of a breathing cycle of the patient, and computing a new target flow rate profile based on the at least one value of nasal pressure.

15. The method of claim 14, wherein estimating at least one value of nasal pressure of the patient over an inspiratory portion of the patient's breathing cycle comprises:

receiving a measure of pressure and adjusting the measure of pressure according to a characteristic function of an air circuit of the respiratory flow therapy device through which the pressure is measured.

16. The method of claim 15, wherein the characteristic function comprises a measured flow value and a pressure drop value.

17. The method of claim 14, wherein computing the new target flow rate profile comprises:

controlling adjustment to the peak inspiratory flow rate based on the at least one nasal pressure value, computing a new minimum inspiratory flow rate profile of the patient from the adjusted peak inspiratory flow rate, and computing the new target flow rate profile using the margin function.

18. The method of claim 17, wherein controlling adjustment to the peak inspiratory flow rate comprises (a) decreasing the peak inspiratory flow rate if the at least one nasal pressure value is above a threshold target; and/or (b) increasing the peak inspiratory flow rate if the at least one nasal pressure value is below a threshold target.

19. The method of claim 1, wherein computing the target flow rate profile comprises receiving estimated breath timing parameters.

20. The method of claim 19, wherein the estimated breath timing parameters comprise an estimated breathing rate and/or an estimated inspiratory time.

21. The method of claim 19, further comprising computing the estimated breath timing parameters by computing impedance or conductance from pressure and flow signals.

22. The method of claim 21, further comprising generating a dynamic impedance signal or dynamic conductance signal with the computed impedance or conductance respectively.

23. The method of claim 22, further comprising determining trigger and/or cycling points from the dynamic impedance signal or the dynamic conductance signal.

24. The method of claim 1, further comprising controlling an oxygen source to add supplementary oxygen to the generated flow of air.

25. The method of claim 24, wherein the supplementary oxygen is added in pulsed oxygen delivery (POD) mode.

26. The method of claim 1, further comprising conditioning, by a humidifier of the respiratory flow therapy device, the generated flow of air.

27. A processor-readable medium, comprising processor-executable instructions stored thereon which, when executed by a processor of a controller, cause the controller to control setting of a respiratory flow therapy device for an anti-infection therapy according to the method of claim 1.

28. An anti-infection therapy device comprising:

a pressure generator configured to generate a flow of air at a controllable flow rate to a patient interface; and a controller comprising one or more processors and a memory, the one or more processors configured to execute program instructions stored in the memory, the program instructions configured to perform the method of claim 1.

29. An anti-infection therapy device comprising:

a pressure generator configured to generate a flow of air at a controllable flow rate to a patient interface; and a controller configured to:

compute a target flow rate profile for a patient using a margin function of the patient's breathing, wherein computing the target flow rate profile during inspiration comprises adding the margin function to a minimum inspiratory flow rate profile of the patient's inspiration such that the target flow rate profile exceeds, according to the margin function, the minimum inspiratory flow rate profile, wherein the computing fits a template function, the template function having a shape, to the patient's peak inspiratory flow rate and an inspiratory time to generate the minimum inspiratory flow rate profile; and control setting of the pressure generator to generate a flow of air to the patient interface according to the target flow rate profile, wherein the generation is in synchrony with a sensed parameter that is indicative of a breathing cycle of the patient.

30. The anti-infection therapy device of claim 29, further comprising an oxygen source configured to add supplementary oxygen to the generated flow of air.

31. The anti-infection therapy device of claim 30, wherein the oxygen source is configured to add the supplementary oxygen in pulsed oxygen delivery (POD) mode.

32. The anti-infection therapy device of claim 29, further comprising a humidifier configured to condition the generated flow of air.

33. Anti-infection therapy apparatus comprising:

means for generating a flow of air at a controllable flow rate to a patient interface;

means for computing a target flow rate profile for a patient using a margin function of the patient's breathing, wherein computing the target flow rate profile during inspiration comprises adding the margin function to a minimum inspiratory flow rate profile of the patient's inspiration such that the target flow rate profile exceeds, according to the margin function, the minimum inspiratory flow rate profile, wherein the computing fits a template function, the template function having a shape, to the patient's peak inspiratory flow rate and inspiratory time to generate the minimum inspiratory flow rate profile; and means for controlling the means for generating to generate the flow of air according to the target flow rate profile, wherein the generation is in synchrony with a sensed parameter that is indicative of a breathing cycle of the patient.

34. The method of claim 1, wherein the template function is a sinusoidal half-wave.

\* \* \* \* \*